(12) United States Patent
Thurston et al.

(10) Patent No.: US 7,407,951 B2
(45) Date of Patent: Aug. 5, 2008

(54) PYRROLOBENZODIAZEPINES

(75) Inventors: David Edwin Thurston, London (GB); Philip Wilson Howard, London (GB)

(73) Assignee: Spirogen Limited, Ryde, Isle of Wight (GB)

( * ) Notice: Subject to any disclaimer, the term of this patent is extended or adjusted under 35 U.S.C. 154(b) by 0 days.

(21) Appl. No.: 10/534,825

(22) PCT Filed: Nov. 14, 2003

(86) PCT No.: PCT/GB03/04963

§ 371 (c)(1), (2), (4) Date: Oct. 20, 2005

(87) PCT Pub. No.: WO2004/043963

PCT Pub. Date: May 27, 2004

(65) Prior Publication Data

US 2006/0128693 A1 Jun. 15, 2006

(30) Foreign Application Priority Data

Nov. 14, 2002 (GB) .................. 0226593.2

(51) Int. Cl.
C07D 487/04 (2006.01)
A61K 31/551 (2006.01)
A61P 35/00 (2006.01)

(52) U.S. Cl. .................. 514/220; 540/496

(58) Field of Classification Search .......... 540/496; 514/220
See application file for complete search history.

(56) References Cited

U.S. PATENT DOCUMENTS

| | | |
|---|---|---|
| 3,523,941 A | 8/1970 | Leimgruber et al. |
| 3,524,849 A | 8/1970 | Batcho et al. |
| 4,185,016 A | 1/1980 | Takanabe et al. |
| 4,239,683 A | 12/1980 | Takanabe et al. |
| 4,309,437 A | 1/1982 | Ueda et al. |
| 5,143,854 A | 9/1992 | Pirrung et al. |
| 5,545,568 A | 8/1996 | Ellman et al. |
| 6,562,806 B1 | 5/2003 | Thurston et al. |
| 6,608,192 B1 | 8/2003 | Thurston et al. |
| 6,660,856 B2 | 12/2003 | Wang |
| 6,747,144 B1 | 6/2004 | Thurston et al. |
| 2003/0120069 A1 | 6/2003 | Thurston et al. |
| 2003/0195196 A1 | 10/2003 | Thurston et al. |
| 2004/0092736 A1 | 5/2004 | Thurston et al. |
| 2004/0198722 A1 | 10/2004 | Thurston et al. |

FOREIGN PATENT DOCUMENTS

| | | |
|---|---|---|
| EP | 0239400 A2 | 9/1987 |
| EP | 1193270 | 4/2002 |
| FR | 2027356 | 12/1969 |
| FR | 2586683 | 3/1987 |
| GB | 1299198 | 12/1972 |
| GB | 2053894 | 2/1981 |
| JP | 53-82792 | 7/1978 |
| JP | 57131791 | 8/1982 |
| JP | 58180487 A | 10/1983 |
| WO | WO 88/04659 | 6/1988 |
| WO | WO 88/07378 | 10/1988 |
| WO | WO 89/10140 | 11/1989 |
| WO | WO 91/16324 | 10/1991 |
| WO | WO 92/19620 | 11/1992 |
| WO | WO 93/08288 | 4/1993 |
| WO | WO 93/18045 | 9/1993 |
| WO | WO 96/23497 | 8/1996 |
| WO | WO 97/01560 | 1/1997 |
| WO | WO 97/07097 | 2/1997 |
| WO | WO 98/11101 | 3/1998 |
| WO | WO 98/12197 | 3/1998 |
| WO | WO 99/29642 | 6/1999 |
| WO | WO 99/46244 | 9/1999 |
| WO | WO 00/12506 | 3/2000 |
| WO | WO 00/12507 | 3/2000 |
| WO | WO 00/12508 | 3/2000 |
| WO | WO 00/12509 | 3/2000 |
| WO | WO 00/64864 | 11/2000 |
| WO | WO 2004/043963 | 5/2004 |
| WO | WO 2005/023814 | 3/2005 |
| WO | WO 2005/040170 | 5/2005 |
| WO | WO 2005/085251 | 9/2005 |

OTHER PUBLICATIONS

Albericio, F. et al., "NPE-Resin, A New Approach to the Solid-Phase Synthesis of Protected Peptides and Oligonucleotides II. Synthesis of Protected Peptides[1,2]," *Tetrahedron Letters*, 32:1515-1518 (1991).

(Continued)

*Primary Examiner*—Bruck Kifle
(74) *Attorney, Agent, or Firm*—Michael Best & Friedrich LLP

(57) ABSTRACT

Compounds of formula (I): formula (I) and salts, solvates, chemically protected forms, and prodrugs thereof, are disclosed wherein $R^2$ is selected from: an optionally substituted napthyl group; an optionally substituted thiophenyl or furanyl group; and a phenyl group substituted by: one or more chloro or fluoro groups; an ethyl or propyl group; a 4-t-butyl group; a 2-methyl group; or two methyl groups in the 2- and 6-positions.

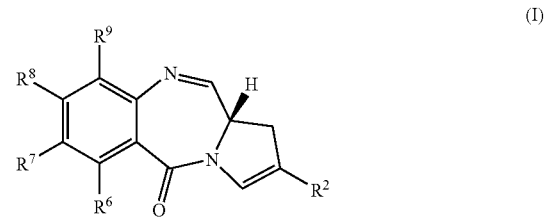

(I)

7 Claims, No Drawings

OTHER PUBLICATIONS

Albericio, F. et al., "NPE-resin, a new approach to the solid-phase synthesis of protected peptides and oligonucleotides," *Peptides* 1990, Proc. 21.sub.st Eur. Pept. Symp., 134-136 (1990).

Althius, T. H. and Hess, H. J., "Synthesis and Identification of the Major Metabolites of Prazosin Formed in Dog and Rat,"0 *J. Medicinal Chem.*, 20(1), 146-148 (1977).

Arima et al., "Studies on Tomaymycin, a New Antibiotic. I. Isolation and Properties of Tomaymycin," *J. Antibiotics*, 25, 437-444 (1972).

Aristoff, J. and Johnson, P., "Synthesis of CBI-PDE-I-Dimer, the Benzannelated Analogue of CC-1065," *J. Org. Chem.*, 57, 6234-6239 (1992).

Bagshawe et al., "Antibody-Enzyme Conjugates Can Generate Cytotoxic Drugs from Inactive Precursors at Tumor Sites," *Antibody, Immunoconjugates, and Radiopharmaceuticals*, 4, 915-922 (1991).

Baraldi, P.G. et al., "Design, synthesis and biological activity of a pyrrolo[2,1-c][1,4]benzodiazepine (PBD)-distamycin hybrid," *Bioorganic & Medicinal Chemistry Letters*, vol. 8, No. 21, 3019-3024 (1998).

Baraldi, P.G. et al., "Synthesis, in Vitro Antiproliferative Activity, and DNA-Binding Properties of Hybrid Molecules Containing Pyrrolo[2,1-c][1,4]benzodiazepine and Minor-Groove-Binding Oligopyrrole Carriers," *J. Med. Chem.*, 42, 5131-5141 (1999).

Bayley, H. et al., "Photoactivatable drugs," *TIPS*, 8, 138-143 (1987).

Berry, J. M. et al., "Solid-phase synthesis of DNA-interactive pyrrolo[2,1-c][1,4]benzodiazepines," *Tetrahedron Letters*, 41, 6171-6174 (2000).

Bi, Y. et al., "Building blocks for peptide and carbamate libraries", *Bioorganic & Medicinal Chemistry Letters*, vol. 6, No. 19, 2299-2300 (1996).

Bi, Y., et al., "Building blocks for peptide and carbamate libraries," *Chemical Abstracts*, vol. 125, No. 23, 1013 (1996).

Boger et al., "CC-1065 and the Duocarmycins: Synthetic Studies," *Chem. Rev.*, 97, 787-828 (1997).

Bose et al., "New Approaches to Pyrrolo[2,1-c][1,4]benzodiazepines: Synthesis, DNA-binding and cytotoxicity of DC-81," *Tetrahedron*, 48, 751-758 (1992).

Bose, D.S. et al., "Rational Design of a Highly Efficient Irreversible DNA Interstrand Cross-Linking Agent Based on the Pyrrolobenzodiazepine Ring System," *J. Am. Chem. Soc.*, 114, 4939-4941 (1992).

Bridges, R.J. et al., "Conformationally Defined Neurotransmitter Analogues. Selective Inhibition of Glutamate Uptake by One Pyrrolidine-2,4-dicarboxylate Diastereomer," *J. Med. Chem.*, 34, 717-725 (1991).

Brown, S.C. et al., "NMR Solution Structure of a Peptide Nucleic Acid Complexed with RNA," *Science*, 265, 777-780 (1994).

Bundgaard, H., "Design and Application of Prodrugs," *A Textbook of Drug Design and Development*, eds Krogsgaard-Lassen, P., and Bundgaard, H., Harwood Academic Press, 113-135 (1991).

Burgess, K. et al., "Solid Phase Synthesis of Oligoureas", *J.Ame. Chem. Soc.*, 119: 1556-1564 (1997).

Burgess, K et al., "Solid Phase Synthesis of Unnatural Biopolymers Containing Repeating Urea Units," *Agnew Chem. Int. Ed. Engl*, 34, No. 8:907-909 (1995).

Carruth, J.A.S., "Clinical applications for photodynamic therapy," *J. Photochem Photobiol.*, 9, 396-397 (1991).

Cho, C Y et al., "An Unnatural Biopolymer", *Science*, 261: 1303-1305 (1993).

Courtney, S. M. et al., "A new convenient procedure for the synthesis of pyrrolo[2,1-c][1,4]benzodiazepines", *Tetrahedron Letters*, vol. 34, No. 33, 5327-28 (1993).

Culver et al., "In Vivo Gene Transfer with Retroviral Vector-Producer Cells for Treatment of Experimental Brain Tumors," *Science*, 256, 1550-1552 (1992).

Dalton, S. and Treisman, R, "Characterization of SAP-1, a Protein Recruited by Serum Response Factor to the *c-fos* Serum Response Element," *Cell*, 68, 597-612 (1992).

Damayanthi, Y., et al., "Design and synthesis of novel pyrrolo [2,1-c][1,4] benzodiazepine-Lexitropsin Conjugates," *J. Org. Chem.*, 64, 290-292 (1999).

Dangles, O. et al., "Selective Cleavage of the Allyl and Allyloxycarbonyl Groups through Palladium-Catalyzed Hydrostannolysis with Tributyltin Hydride. Application to the Selective Protection-Deprotection of Amino Acid Derivatives and in Peptide Synthesis," *J. Org. Chem.*, 52, 4984-4993 (1987).

Dressman, B.A., et al., "Solid Phase Synthesis of Hydantoins Using a Carbamate Linker and a Novel Cyclization/Cleavage Step," *Tetrahedron Letters*, 937-940 (1996).

Drost, K.J. and Cava, M.P., "A Photochemically Based Synthesis of the Benzannelated Analogue of the CC-1065 A Unit," *J. Org. Chem.*, 56:2240-2224 (1991).

Eashoo, M. et al., "Fibers from a Low Dielectric Constant Fluorinated Polyimide: Solution Spinning and Morphology Control," *J. Polymer Science*, 35:173-185 (1997).

Edman, P. and Begg, G., "A Protein Sequenator," *Eur. J. Biochem.*, 1, 80-91 (1967).

Egholm, M et al., "Peptide Nucleic Acids (PNA). Oligonucleotide Analogues with an Achiral Peptide Backbone," *J. Am. Chem. Soc.*, 114, 1895-1897 (1992).

Egholm, M et al., "PNA hybridizes to complementary oligonucleotides obeying the Watson-Crick hydrogen-bonding rules," *Nature*, 365, 566-568 (1993).

Englehardt et al., "Direct gene transfer of human CFTR into human bronchial epithelia of xenografts with E1-deleted adenoviruses," *Nature Genetics*, 4, 27-34 (1993).

Farmer, J.D. et al., "DNA binding properties of a new class of linked anthramycin analogs,", *Chemical Abstracts*, Abstract No. 239940r, vol. 114, No. 25, 25 899-903 (1991).

Figliozzi, G.M. et al., "Synthesis of N-substituted Glycine Peptoid Libraries," *Methods in Enzymology*, 267:437-447 (1996).

Foloppe, M.P. et al., "DNA-binding properties of pyrrolo[2,1-c][1,4]benzodiazephine N10-C11 amidines," *Eur. J. Med. Chem.*, 31, 407-410 (1996).

Fujisawa Pharmaceutical Co., Ltd., Abstract No. 139983k, "Benzodiazepine derivatives", *Chemical Abstracts*, vol. 99, No. 17, 603 (1983).

Fujisawa Pharmaceutical Co., Ltd., Abstract No. 72145x, "Benzodiazepine derivatives", *Chemical Abstracts*, vol. 98, No. 9, 638 (1983).

Fujisawa Pharmaceutical Co. Ltd., "Benzodiazepine derivatives," *SciFinder Scholar*, 2-3 (2002).

Fukuyama, T. et al., "Total Synthesis of (+)-Porothramycin B," *Tetrahedron Letters*, vol. 34, 16, 2577-2580 (1993).

Furka, A. et al., "General method for rapid synthesis of multicomponent peptide mixtures," *Int. J. Peptide Protein Res.*, 37, 487-493 (1991).

Garcia-Echeverria, C., "A Base Labile Handle for Solid Phase Organic Chemistry", *Tetrahedron Letters*, 38,52, 8933-8934 (1997).

Grant, R. et al., *Grant and Hackh's Chemical Dictionary*, McGraw-Hill Book Company, 282 (1987).

Greene, T.W. and Wuts, P.G.M., *Protective Groups on Organic Synthesis*, John Wiley & Sons, 2nd ed., Ch 7, 315-345 (1991).

Gregson, S. et al., "Synthesis of a novel C2/C2'-exo unsaturated pyrrolobenzodiazepine cross-linking agent with remarkable DNA binding affinity and cytotoxicity," *Chemical Communications*, 797-798 (1999).

Gregson, S.J. et al., "Design, Synthesis and Evaluation of a Novel Pyrrolobenzodiazepine DNA-Interactive Agent with Highly Efficient Cross-Linking Ability and Potent Cytotoxicity", *J. Med. Chem.*, 44: 737-748 (2001).

Gregson, S.J. et al., "Effect of C2-*exo* Unsaturation on the Cytotoxicity and DNA-Binding Reactivity of Pyrrolo[2,1-c]1,4benzodiazepines", *Bioorganic & Medicinal Chemistry Letters*, 10: 1845-1847 (2000).

Guiotto, A. et al., "Synthesis of novel C7-aryl substituted pyrrolo[2,1-c][1,4]benzodiazepines (PBDs) via Pro-N10-troc protection and suzuki coupling," *Bioorganic & Medicinal Chemistry Letters*, 8, No. 21, 3017-3018 (1998).

Hara et al., "DC 102, a new glycosidic pyrrolo(1,4)benzodiazepine antibiotic produced by *streptomyces* sp.", *J. Antibiotics*, 41, 702-704 (1988).

Hauske, J. R. and Dorff, P., "Solid Phase CBZ Chloride Equivalent. A New Matrix Specific Linker", *Tetrahedron Letters*, 36, 10, 1589-1592 (1995).

Hocart et al., "Highly potent cyclic disulfide antagonists of somatostatin," *J. of Medicinal Chem.*, 42:11 (1999).

Hochlowski, J. et al., "Abbeymycin, a new anthramycin-type antibiotic produced by a streptomycete," *J. Antibiotics*, 40, 145-148 (1987).

Holmes, C.P. and Jones, D.G., "Reagents for Combinatorial Organic Synthesis: Development of a New O-Nitrobenzyl Photolabile Linker for Solid Phase Synthesis", *J. Org. Chem.*, 60, 2318-2319 (1995).

Huber, B. et al., "Retroviral-mediated gene therapy fot the treatment of hepatocellular carcinoma: An innovative approach for cancer therapy," *Proc. Natl. Acad. Sci. USA*, 88, 8039-8043 (1991).

Hurley, L. and Needham-Vandevanter, D., "Covalent Binding of Antitumor Antibiotics in the Minor Groove of DNA. Mechanism of Action of CC-1065 and the Pyrrolo(1,4)benzodiazepines," *Acc. Chem. Res.*, 19, 230-237 (1986).

Itoh et al., "Sibanomicin, a new pyrrolo(1,4)benzodiazepine antitumor antibiotic produced by a *micromonospora* sp." *J. Antibiotics*, 41, 1281-1284 (1988).

Jenkins, T.C. et al., "Structure of a Covalent DNA Minor Groove Adduct with a Pyrrolobenzodiazepine Dimer: Evidence for Sequence-Specific Interstrand Cross-Linking," *J. Med. Chem.*, 37, 4529-4537 (1994).

Jungheim, L.N. and Shepherd, T.A., "Design of Antitumor Prodrugs: Substrates for Antibody Targeted Enzymes," *Am. Chem. Soc. Chem. Rev.*, 94, 1553-1566 (1994).

Kamal, A., et al., "An Efficient Synthesis of Pyrrolo[2,1-c][1,4] Benzodiazepine Antibiotics via Reductive Cyclization," *Bioorg. Med. Chem. Ltrs*, No. 14, 1825-1828 (1997).

Kamal, A., et al., "Synthesis of Pyrrolo [2,1-c][1,4]-Benzodiazepene Antibiotics: Oxidation of Cyclic Secondary Amine with TPAP", *Tetrahedron*, v. 53, No. 9, 3223-3230 (1997).

Kapoor, T.M. et al., "Exploring the Specificity Pockets of Two Homologous SH3 Domains Using Structure-Based, Split-Pool Synthesis and Affinity-Based Selection," *J. Am. Chem. Soc.* 120:23-29 (1998).

Katritzky et al., *Heterocyclic Chemistry*, John Wiley & Sons, Inc., 247-253 (1960).

Kennedy, J.C. and Pottier, R.H., "Endogenous protoporphyrin IX, a clinical useful photosensitiser for photodynamic therapy," *J. Photochem Photobiol*, 14, 275-292 (1992).

Kohn, K., "Anthramycin," *Antibiotics III*, Springer-Verlag, NY, 3-11 (1975).

Konishi, M. et al., "Chicamycin, a new antitumor antibiotic II. Structure determination of chicamycins A and B," *J. Antibiotics*, 37, 200-206 (1984).

Kunimoto et al., "Mazethramycin, a new member of anthramycin group antibiotics," *J. Antibiotics*, 33, 665-667 (1980).

Kunz, H. and Dombo, B., "Solid phase synthesis of peptide and Glycopeptides on polymeric Supports with Allylic Anchor Groups," *Angew Chem. Int. Ed. Engl*, 5, 711-713 (1988).

Kuzmich, S. et al., "Increased levels of glutathione S-transferase π transcript as a mechanism of resistance to ethacrynic acid," *Journal of Biochemistry*, 281, 219-224 (1992).

Langley, D,R, and Thurston, D.E., "A versatile and efficient synthesis of carbinolamine-containing pyrrolo[1,4]benzodiaxepines via the cyclization of N-92-aminobenziyl)pyrrolidine-2-carboxaldehyde diethyl thioacetals: total synthesis of prothracarcin," *J. Org. Chem.*, 91-97 (1987).

Leber, J.D. et al., "A revised structure for sibiromycin," *J. Am. Chem. Soc.*, 110, 2992-2993 (1988).

Leimgruber, W. et al., "Isolation and characterization of anthramycin, a new antitumor antibiotic," *J. Am. Chem. Soc.*, 87, 5791-5793 (1965).

Leimgruber, W. et al., "The structure of anthramycin," *J. Am. Chem. Soc.*, 87, 5793-5795 (1965).

Leimgruber, W. et al., "Total synthesis of anthramycin," *J. Am. Chem. Soc.*, 90, 5641-5643 (1968).

Lescrinier, T. et al., "DNA-binding Ligands from Peptide Libraries Containing Unnatural Amino Acids," *Chem. Eur. J.*, 4, 3, 425-433 (1998).

Lewis A.D. et al., "Glutathione and glutathione-dependent enzymes in ovatian adenocarcinoma cell lines derived from a patient before and after the onset of drug resistance; intrinsic differences and cell cycle effects," *Carcinogensis*, 9, 1983-1287 (1988).

Lown et al., "Molecular Mechanism of binding of pyrrolo(1,4)benzodiazepine antitumour agents to deoxyribonucleic acid—anthramycin and tomaymycin," Biochem. Pharmacol. (1979), 28 (13), 2017-2026; and abstract no. 51709.

Mizushima, S. and Nagata, S., "pEF-BOS, a powerful mammalian expression vector," *Nucl. Acids Res.*, 18, 5322 (1990).

Monks, A. et al., "Feasibility of High-Flux Anticancer Drug Screen Using a Diverse Panel of Cultured Human Tumor Cell Lines," *Journal of National Cancer Institute*, 83, 757-766 (1991).

Moran, E.J. et al., "Novel Biopolymers for Drug Discovery: Biopolymers", *Peptide Science*, John Wiley and Sons, 37: 213-19 (1995).

Morgan, R.A. and Anderson, W.F., "Human Gene Therapy," *Annu. Rev. Biochem.*, 62, 191-217 (1993).

Mosmann, T., "Rapid Colorimetric Assay for Cellular Growth and Survival: Application to Proliferation and Cytotoxicity Assays," *J. Immunological Methods*, 65, 55-63 (1983).

Mullen, D.G. and Barany, G., "A New Fluoridolyzable Anchoring Linkage for Orthogonal Solid-Phase Peptide Synthesis: Design, Preparation, and Application of the N-(3 or 4)-[[4-(hydroxymethyl) phenoxy]-tert-butylphenylsily]phenyl Pentanedioic Acid Monoamide (Pbs) Handle", *J. Org. Chem.*, 53, 5240-5248 (1988).

Nagasaka, T. and Koseki, Y, "Stereoselective Synthesis of Tilicalline," *Journal of Organic Chemistry*, vol. 63, No. 20, 6797-6801 (1998).

Nagasaka, T. et al., "Stereoselective Synthesis of Tilivalline," *Tetrahedron Letters*, 30:14, 1871-1872 (1989).

Nicolaou, K.C. et al., "Designed Enediynes: A New Class of DNA-Cleaving Molecules with Potent and Selective Anticancer Activity," *Science*, 256, 1172-1178 (1992).

Nielson, P.E. et al., "Sequence-Selective Recognition of DNA by Strand Displacement with a Thymine-Substituted Polyamide," *Science*, 254, 1497-1500 (1991).

O'Neil, I.A., et al., "The Synthesis of Functionalized Pyrrolo-[2,1-c][1,4]-Benzodiazepines," *Synlett*, 75-78 (1997).

O'Neil, Chemical Abstract No. 171573p, "synthesis of Functionalized Pyrrolo-[2,1-c][1,4]-Benzodiazepines", *Chemical Abstracts*, vol. 126, No. 13, 618 (1997).

O'Neil, I.A. et al., "DPPE: A Convenient Replacement for Triphenylphosphine in the Staudinger and Mitsunobu Reactions", *Tetrahedron Letters*, vol. 39, No. 42, 7787-7790 (1998).

Paikoff, S.J. et al., "The Solid Phase Synthesis of N-Alkylcarbamate Oligomers", *Tetrahedron Letters*, 37, No. 32:5653-5656 (1996).

Pillai, V.N.R., "Photoremovable protecting groups in organic chemistry," *Synthesis*, 1-26 (1980).

Ram, Z. et al., "In Situ Retroviral-mediated Gene Transfer for the Treatment of Brain Tumors in Rats," *Cancer Research*, 53, 83-88 (1993).

Rawal, V.H. et al., "Photocyclization Strategy fot the Synthesis of Antitumor Agent CC-1065: Synthesis of Dideoxy PDE-I and PDE-II. Synthesis of Thiophene and Furan Analogues of Dideoxy PDE-I and PDE-II," *J. Org. Chem.*, 52, 19-28 (1987).

Regula, J. et al., "Photosensitisation and photodynamic therapy of oesophagael, duodenal and colorectal tumours using 5-aminoleavulic acid induced photoporphyrin IX-a pilot study," *Gut*, 36, 67-75 (1995).

Sagnou, M.J. et al., "Design and Synthesis of Novel Pyrrolobenzodiazepine (PDB) Prodrugs for ADEPT and GDEPT," *Bioorganic & Medicinal Chemistry Letters*, 10, 2083-2086 (2000).

Saha, A.K. et al., "Diisopropylsilyl-Linked Oligonucleotide Analogs: Solid-Phase Synthesis and Physiocochemical Properties," *J. Org. Chem.*, 58, 7827-7831 (1993).

Satyam, A. et al., "Design, Synthesis, and Evaluation of Latent Alkylating Agents Activated by Glutathione S-Transferase," *J. Med. Chem.*, 39, 1736-1747 (1996).

Shimizu, K et al., "Prothracarcin, a Novel Antitumor Antibiotic," *J. Antibiotics*, 35, 972-978 (1982).

Simon, R.J. et al., "Peptoids: A Modular Approach to Drug Discovery", *Proc. Natl. Acad. Sci.*, USA,89:9367-9371 (1992).

Soth, M.J. and Nowick, J.S., "Unnatural oligomers and unnatural oligomer libraries", *Curr. Opin. Chem. Biol.*, 1:120-129 (1997).

Star, W.M., "Light delivery and light dosimetry for photodynamic therapy," *Lasers in Medical Science*, 5:107-113 (1990).

Suggs, J.W. et al., "Synthesis and structure of anthramycin analogs via hydride reduction of dilactams," *Tetrahedron Letters*, 26, No. 40, 4871-4874 (1985).

Takeuchi, T. et al., "Neothramycins A and B, New Antitumor Antibiotics," *J. Antibiotics*, 29, 93-96 (1976).

Tew, K.D. and Clapper, M.L., "Glutathione-S-transerase and anticancer drug resistance," *Mechanism of Drug Resistance in Neoplastic Cells*, Woolley, P.V. and Tew, K.D., Eds, Academic Press: Sand Diego, CA 141-159 (1988).

Thurston, D.E. and Thompson, A.S., "The molecular recognition of DNA," *Chem. Brit.*, 26, 767-772 (1990).

Thurston, D.E. and Bose, D.S., "Synthesis of DNA-Interactive Pyrrolo[2,1-c][1,4]benzodiazepines," *Chem. Rev.*, 94:433-465 (1994).

Thurston, D.E., "Advances in the study of Pyrrolo[2,1-c][1,4]benzodiazepine (PBD) Antitumour Antibiotics", *Molecular Aspects of Antincances Drug-DNA Interaction*, Neidle, S. and Waring, M.J., Eds.; Macmillan Press Ltd, 1:54-88 (1993).

Thurston, D.E. et al., "Effect of A-ring modifications on the DNA-binding behavior and cytotoxicity of pyrrolo[2,1-c][1,4]benzodiazepines", *Journal of Medicinal Chemistry*, 42:1951-1964 (1999).

Thurston, D.E. et al., "Synthesis of Sequence-selective C8-linked Pyrrolo [2,1-c][1,4] Benzodiazepine DNA Interstrand Cross-linking Agent," *J. Org. Chem.*, 61:8141-8147 (1996).

Thurston, D.E. et al., "Synthesis of a novel CG-specific covalent-binding DNA affinity-cleavage agent based on pyrrolobenzodiazepines (PBDs)," Chemical Communications, 563-565 (1996).

Tsunakawa, M. et al., "Porothramycin, a new antibiotic of the anthramycin group: Production, isolation, structure and biological activity," *J. Antibiotics*, 41:1366-1373 (1988).

Umezawa, H. et al., Chemical Abstract No. 4427a, "Mazethramycins" *Chemical Abstracts*, vol. 90, No. 1, 428 (1979).

Umezawa, H. et al., "Mazethramycins," *SciFinder Scholar*, 2-3 (2002).

Wilson, S.C. et al., "Design and Synthesis of a Novel Epoxide-Containing Pyrrolo [2,1-c][1,4]benzodiazepine (PBD) via a New Cyclization Procedure," *Tetrahedron Letters*, 36, No. 35, 6333-6336 (1995).

Wilson, S.C. et al., "Design, Synthesis, and Evaluation of a Novel Sequence-Selective Epoxide-Containing DNA Cross-Linking Agent Based on the Pyrrolo[2,1-*c*][1,4]benzodiazepine System", *J. Med. Chem.* 42:4028-4041 (1999).

Zuckerman, R.N. et al., "Discovery of Nanomolecular Ligands for 7-Transmembrane G-Protein-Coupled Receptors from a Diverse N-(Substituted) glycine Peptoid Library", *J. Med. Chem.*, 37:2678-2685 (1994).

*Dictionary of Science and Technology*, Professor P.M.B. Walker ed. Larousse plc., pp. 63, 457, 523 (1995).

Adams et al., "Molecular modelling of a sequence-specific DNA-binding agent based on the pyrrolo[2,1-c][1,4]benzodiazepines," Pharm. Pharmacol. Commun. (1999) 5:555-560.

Baraldi, P.G. et al., "[2,1-c][1,4]benzodiazepine (PBD)-distamycin hybrid inhibits DNA binding to transcription factor Sp1," Nucleotides and Nucleic Acids (2000) 19(8):1219-1229.

Berge et al., " Pharmaceutical Salts," J. Pharm. Sci. (1977) 66:1-19.

Borgatti, M. et al., "Inhibition of NF-kB/DNA ineractions and HIV-1 LTR directed transcription by hybrid molecules containing pyrrolo [2,1-c][1,4] benzodiazepine (PBD) and oligopyrrole carriers," Drug Development Research (2003) 60(3):173-185.

Bose, D.S. et al., "Effect of linker length on DNA-binding affinity, cross-linking efficiency and cytotoxicity of C8 linked pyrrolobenzodiazepine dimers," J. Chem. Soc. Chem. Commun. (1992) 20:1518-1520.

Chen, Z. et al., "A novel approach to the synthesis of cytotoxic C2-C3 unsaturated pyrrolo[2,1-c][1,4]benzodiazepines (PBDs) with conjugated acrylyl C2-substituents," Biorg. Med. Chem. Lett. (2004) 14:1547-1549.

Cooper, N. et al., "Synthesis of novel PBDs an anti-tumour agents," Chem. Commun. (2002) 16:1764-1765.

De Groot, FMH et al., "Synthesis and biological evaluation of 2'-carbamate-linked 2'-carbonate-linked prodrugs of paclitaxel: selective activation by the tumor-associated protease plasmin," J. Med. Chem. (2000) 43(16):3093-3102.

De Groot, FMH et al., "Novel 20-carbonate linked prodrugs of camptothecin and 9-aminocamptothecin designed for activation by tumour-associated plasmin," Biorg. Med. Chem. Lett. (2002) 12(17):2371-2376.

Dubowchik, G.M. et al., "Cathepsin B-sensitive dipeptide prodrugs. 1. A model study of structural requirements for efficient release of doxorubicin," Biorg. Med. Chem. Lett. (1998) 8:3341-3346.

Dubowchik, G.M. et al., "Cathepsin B-sensitive dipepide prodrugs. 2. Models of anticancer drugs paclitaxel (Taxol), Mitomycin C and Doxorubicin," Biorg. Med. Chem. Lett. (1998) 8:3347-3352.

Dubowchik and Walker, "Receptor-mediated and enzyme-dependent targeting of cytotoxic anticancer drugs," Pharmacology and Therapeutics (1999) 83:67-123.

Garsky et al., "The synthesis of a prodrug of doxorubicin designed to provide reduced systemic toxicity and greater target efficacy," J. Med. Chem. (2001) 44:4216-4224.

Gregson, S.J. et al., "Effect of C2/C3-endo unsaturation on the cytotoxicity and DNA-binding reactivity of pyrrolo-[2,1-c][1,4]-benzodiazepines," Bioorg. Med. Chem. Lett. (2000) 10(16):1849-1851.

Gregson, S.J. et al., "Linker length modulates DNA cross-linking reactivity and cytotoxic potency of C8/C8[1] ether-linked C2-exo-unsaturated pyrrolo[2,1-c][1,4]benzodiazepine (PBD) dimers," J. Med. Chem. (2004) 1161-1174.

Gregson, S.J. et al., "Synthesis of the first example of a C2-C3/C2'-C3'-endo unsaturated pyrrolo[2,1-c][1,4]benzodiazepine dimer," Biorg. Med. Chem. Lett. (2001) 11:2859-2862.

Gregson, S.J. et al., "Synthesis of the first examples of A-C8/C-C2 amide-linked pyrrolo[2,1-c][1,4]benzodiazepine dimers," Biorg. Med. Chem. Lett. (2003) 13:2277-2280.

Hamburger, A. W. et al., "Primary bioassay of human tumor stem cells," Science (1977) 197:461-643.

Jakobsen et al., "Design, synthesis, and pharmacological evaluation of thapsigargin analogues for targeting apoptosis to prostatic cancer cells," J. Med. Chem. (2001) 44:4696-4703.

Kamal et al., "Synthesis and DNA-binding affinity of A-C8/C-C2 alkoxyamido-linked pyrrolo[2,1-c][1,4]benzodiazepine dimers" Biorg. Med. Chem. Lett. (2003) 13(22):3955-3958.

Kamal, et al., "Synthesis of pyrrolo[2,1-c][1,4]benzodiazepines via reductive cyclization of w-azido carbonyl compounds by TMSI: an efficient preparation of antibiotic DC-81 and its dimers," Biorg. Med. Chem. Lett. (2000) 10:2311-2313.

Kaneko, T. et al., "Bicyclic and tricyclic analogues of anthramycin," J. Med. Chem. (1985) 28:388-392.

Kang, G.-D. et al., "Synthesis of a novel C2-aryl substituted 1,2-unsaturated pyrrolobenzodiazepine," Chem. Commun. (2003) 1688-1689.

Kumar, R. et al., "Synthesis and antitumor cytotoxicity evaluation of novel pyrrolo[2,1-c][1,4]benzodiazepine imidazole containing polyamide conjugates," Oncology Research (2003) 13(4):221-223.

Kumar, R. et al., "Design and synthesis of novel pyrrolo[2,1-c][1,4]benzodiazepine—imidazole containing polyamide conjugates," Heterocyclic Communications (2002) 81(1):19-26.

Kumar, R. et al., "Design, synthesis and in vitro cytotoxicity studies of novel pyrrolo [2,1][1,4]benzodiazepine-glycosylated pyrrole and imidazole polyamide conjugates," Org. Biomol. Chem. (2003) 1(19):3327-3342.

Langlois, N. et al., "Synthesis and cytotoxicity on sensitive and doxorubicin-resistant cell lines of new pyrrolo[2,1-c][1,4]benzodiazepines related to anthramycin," J. Med. Chem. (2001) 44:3754-3757.

Lipshutz, B.H. et al., "Pd(II)_Catalyzed Acetal/Ehtal Hydrolysis/Exchange Reactions," Tetrahedron Lett. (1985) 26(6):705-708.

Mhaka et al., "A 5-fluorodeoxyuridine prodrug as targeted therapy for prostate cancer," Biorg. Med. Chem. Lett. (2002) 12(17:2459-2461.

Mischiati, C. et al., "Binding of hybrid molecules containing pyrrolo[2,1-c][1,4]benzodiazepine (PBD) and oligopyrrole carriers to the human immunodeficiency type 1 virus TAR-RNA," Biochem. Pharmacol. (2004) 67(3):401-410.

Mori, M. et al., "Total syntheses of prothracarcin and tomaymycin by use of palladium catalyzed carbonylation," Tetrahedron (1986) 42(14):3793-3806.

Mountzouris, J.A. et al., "Comparison of a DSB-120 DNA interstrand cross-linked adduct with the corresponding bis-Tomamycin adduct," J. Med. Chem. (1994) 37:3132-3140.

Niculescu-Duvaz, D. et al., "Self-immolative nitrogen mustard prodrugs for suicide gene therapy," J. Med. Chem. (1998) 41(26):5297-5309.

Reddy et al., "Design, synthesis and in vitro cytotoxicity studies of novel pyrrolo[2,1-c][1,4]benzodiazepine (PBD)-polyamide conjugates and 2,2'-PBD dimers," Ani-Cancer Drug Design (2000) 15(3):225-228.

Smellie, M. et al., "Cellular pharmacology of novel C8-linked anthramycin-baced sequence -selective DNA minor groove cros-linking agents," Br. J. Cancer (1994) 70:48-53.

Smellie, M. et al., "Sequence selective recognition of duplex DNA through covalent interstrand cross-linking," Biochem. (2003) 42:8232-8239.

Thurston, D.E., "Nucleic acid targeting: therapeutic strategies for the 21st century," Brit. J. Cancer (1999) 80(1):65-85.

Tiberghien, A.C. et al., "Application of the stille coupling reaction to the synthesis of C2-substituted endo-exo unsaturated pyrrolo[2,1-c][1,4]benzodiazepines (PBDs),"Biorg. Med. Chem. Lett. (2004) 14:5041-5044.

Wells, G. et al., "Pyrrolobenzodiazepine-polyamide libraries: synthesis and DNA binding selectivity," Proc. Am. Assoc. Canc. Res. (2003) 44:85-86, #452.

Wermuth et al., "Molecular Variations Based on Isosteric Replacements," The Practice of Medicinal Chemistry, Chapter 13 (1996) 203-237.

Williams, M.A. et al., "Synthesis of conformationally constrained DTPA analogues. Incorporation of the ethylenediamine units as aminopyrrolidines," J. Org. Chem. (1994) 59(13):3616-3625.

PYRROLOBENZODIAZEPINES

CROSS-REFERENCE TO RELATED APPLICATIONS

This patent application is a national stage filing under 35 U.S.C. 371 of International Application No. PCT/GB2003/004963, filed on Nov. 14, 2003, which claims foreign priority benefits to Great Britain No. 0226593.2, filed on Nov. 14, 2002.

The present invention relates to pyrrolobenzodiazepines (PBDs), and in particular pyrrolobenzodiazepines having a C2-C3 double bond, an aryl group at the C2 position, and particular substituents on that C2 aryl group.

BACKGROUND TO THE INVENTION

Some pyrrolobenzodiazepines (PBDs) have the ability to recognise and bond to specific sequences of DNA; the preferred sequence is PuGPu. The first PBD antitumour antibiotic, anthramycin, was discovered in 1965 (Leimgruber, et al., *J. Am. Chem. Soc.*, 87, 5793-5795 (1965); Leimgruber, et al., *J. Am. Chem. Soc.*, 87, 5791-5793 (1965)). Since then, a number of naturally occurring PBDs have been reported, and over 10 synthetic routes have been developed to a variety of analogues (Thurston, et al., *Chem. Rev.* 1994, 433-465 (1994)). Family members include abbeymycin (Hochlowski, et al., *J. Antibiotics*, 40, 145-148 (1987)), chicamycin (Konishi, et al., *J. Antibiotics*, 37, 200-206 (1984)), DC-81 (Japanese Patent 58-180 487; Thurston, et al., *Chem. Brit.*, 26, 767-772 (1990); Bose, et al., *Tetrahedron*, 48, 751-758 (1992)), mazethramycin (Kuminoto, et al., *J. Antibiotics*, 33, 665-667 (1980)), neothramycins A and B (Takeuchi, et al., *J. Antibiotics*, 29, 93-96 (1976)), porothramycin (Tsunakawa, et al., *J. Antibiotics*, 41, 1366-1373 (1988)), prothracarcin (Shimizu, et al, *J. Antibiotics*, 29, 2492-2503 (1982); Langley and Thurston, *J. Org. Chem.*, 52, 91-97 (1987)), sibanomicin (DC-102)(Hara, et al., *J. Antibiotics*, 41, 702-704 (1988); Itoh, et al., *J. Antibiotics*, 41, 1281-1284 (1988)), sibiromycin (Leber, et al., *J. Am. Chem. Soc.*, 110, 2992-2993 (1988)) and tomamycin (Arima, et al., *J. Antibiotics*, 25, 437-444 (1972)). PBDs are of the general structure:

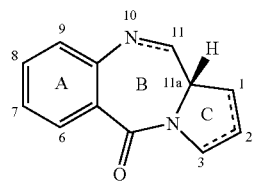

They differ in the number, type and position of substituents, in both their aromatic A rings and pyrrolo C rings, and in the degree of saturation of the C ring. In the B-ring there is either an imine (N=C), a carbinolamine(NH—CH(OH)), or a carbinolamine methyl ether (NH—CH(OMe)) at the N10-C11 position which is the electrophilic centre responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site (Kohn, *In Antibiotics III.* Springer-Verlag, New York, pp. 3-11 (1975); Hurley and Needham-VanDevanter, *Acc. Chem. Res.*, 19, 230-237 (1986)). Their ability to form an adduct in the minor groove, enables them to interfere with DNA processing, hence their use as antitumour agents.

The present inventors have previously disclosed, in WO 00/12508, that the following compounds, amongst many other, are cytotoxic:

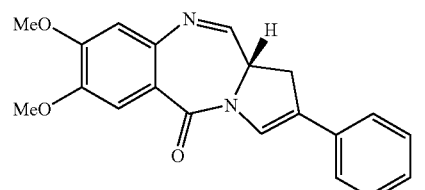

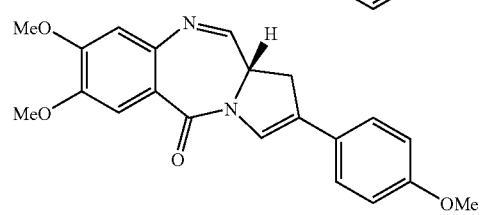

More recently, in Cooper. N., et al., *Chem. Commun.*, 16, 1764-1765 (2002), the following compound was also disclosed as being cytotoxic alongside the compounds shown above.

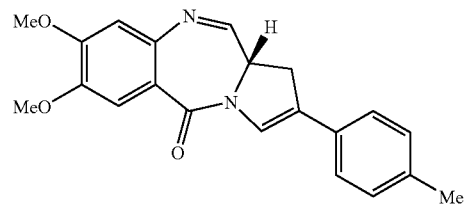

DISCLOSURE OF THE INVENTION

The present inventors have now discovered that a certain class of these compounds exhibit surprising activity against cancer cell lines, compared to the known compounds discussed above.

Therefore, a first aspect of the present invention is a compound of formula (I):

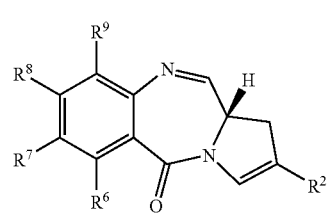

and salts, solvates, chemically protected forms, and prodrugs thereof, wherein:

$R^6$, R7 and $R^9$ are independently selected from H, R, OH, OR, SH, SR, $NH_2$, NHR, NHRR', nitro, $Me_3Sn$ and halo;

where R and R' are independently selected from optionally substituted $C_{1-7}$ alkyl, $C_{3-20}$ heterocyclyl and $C_{5-20}$ aryl groups; $R^8$ is selected from H, R, OH, OR, SH, SR, $NH_2$, NHR, NHRR', nitro, $Me_3Sn$ and halo, or the compound is a dimer with each monomer being of formula (I), where the $R^8$ groups of each monomers form together a dimer bridge having the formula —X—R"—X— linking the monomers, where R" is a $C_{3-12}$ alkylene group, which chain may be interrupted by one or more heteroatoms, e.g. O, S, NH, and/or aromatic rings, e.g. benzene or pyridine, and each X is independently selected from O, S, or NH;

or any pair of adjacent groups from $R^6$ to $R^9$ together form a group —O—$(CH_2)_p$—O—, where p is 1 or 2; and $R^2$ is selected from:
(i) an optionally substituted napthyl group;
(ii) an optionally substituted thiophenyl or furanyl group; and
(iii) a phenyl group substituted by:
 (a) one or more chloro or fluoro groups;
 (b) an ethyl or propyl group;
 (c) a 4-t-butyl group;
 (d) a 2-methyl group;
 (e) two methyl groups in the 2- and 6-positions.

A second aspect of the present invention is the use of a compound of the first aspect of the invention in a method of therapy.

A third aspect of the present invention is a pharmaceutical composition containing a compound of the first aspect of the invention, and a pharmaceutically acceptable carrier or diluent.

A fourth aspect of the present invention provides the use of a compound of the first aspect of the invention in the manufacture of a medicament for treating a proliferative disease.

One of ordinary skill in the art is readily able to determine whether or not a candidate compound treats a proliferative condition for any particular cell type. For example, assays which may conveniently be used to assess the activity offered by a particular compound are described in the examples below.

The term "proliferative disease" pertains to an unwanted or uncontrolled cellular proliferation of excessive or abnormal cells which is undesired, such as, neoplastic or hyperplastic growth, whether in vitro or in vivo.

Examples of proliferative conditions include, but are not limited to, benign, pre-malignant, and malignant cellular proliferation, including but not limited to, neoplasms and tumours (e.g. histocytoma, glioma, astrocyoma, osteoma), cancers (e.g. lung cancer, small cell lung cancer, gastrointestinal cancer, bowel cancer, colon cancer, breast carinoma, ovarian carcinoma, prostate cancer, testicular cancer, liver cancer, kidney cancer, bladder cancer, pancreas cancer, brain cancer, sarcoma, steosarcoma, Kaposi's sarcoma, melanoma), leukemias, psoriasis, one diseases, fibroproliferative disorders (e.g. of connective tissues), and atherosclerosis.

Any type of cell may be treated, including but not limited to, lung, gastrointestinal (including, e.g. bowel, colon), breast (mammary), ovarian, prostate, liver (hepatic), kidney (renal), bladder, pancreas, brain, and skin.

Substituents

The phrase "optionally substituted" as used herein, pertains to a parent group which may be unsubstituted or which may be substituted.

Unless otherwise specified, the term "substituted" as used herein, pertains to a parent group which bears one or more substitutents. The term "substituent" is used herein in the conventional sense and refers to a chemical moiety which is covalently attached to, or if appropriate, fused to, a parent group. A wide variety of substituents are well known, and methods for their formation and introduction into a variety of parent groups are also well known.

Examples of substituents are described in more detail below.

$C_{1-7}$ alkyl: The term "$C_{1-7}$ alkyl" as used herein, pertains to a monovalent moiety obtained by removing a hydrogen atom from a carbon atom of a hydrocarbon compound having from 1 to 7 carbon atoms, which may be aliphatic or alicyclic, and which may be saturated or unsaturated (e.g. partially unsaturated, fully unsaturated). Thus, the term "alkyl" includes the sub-classes alkenyl, alkynyl, cycloalkyl, etc., discussed below.

Examples of saturated alkyl groups include, but are not limited to, methyl ($C_1$), ethyl ($C_2$), propyl ($C_3$), butyl (C4), pentyl ($C_5$), hexyl ($C_6$) and heptyl (C7).

Examples of saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$) and n-heptyl ($C_7$).

Examples of saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

$C_{2-7}$ Alkenyl: The term "$C_{2-7}$ alkenyl" as used herein, pertains to an alkyl group having one or more carbon-carbon double bonds.

Examples of unsaturated alkenyl groups include, but are not limited to, ethenyl (vinyl, —CH=$CH_2$), 1-propenyl (—CH=CH—$CH_3$), 2-propenyl (allyl, —CH—CH=$CH_2$), isopropenyl (1-methylvinyl, —C($CH_3$)=$CH_2$), butenyl ($C_4$), pentenyl ($C_5$), and hexenyl ($C_6$).

$C_{2-7}$ alkynyl: The term "$C_{2-7}$ alkynyl" as used herein, pertains to an alkyl group having one or more carbon-carbon triple bonds.

Examples of unsaturated alkynyl groups include, but are not limited to, ethynyl (ethinyl, —C≡CH) and 2-propynyl (propargyl, —$CH_2$—C≡CH).

$C_{3-7}$ cycloalkyl: The term "$C_{3-7}$ cycloalkyl" as used herein, pertains to an alkyl group which is also a cyclyl group; that is, a monovalent moiety obtained by removing a hydrogen atom from an alicyclic ring atom of a cyclic hydrocarbon (carbocyclic) compound, which moiety has from 3 to 7 carbon atoms, including from 3 to 7 ring atoms.

Examples of cycloalkyl groups include, but are not limited to, those derived from:
saturated monocyclic hydrocarbon compounds:
cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$) and methylcyclohexane ($C_7$);
unsaturated monocyclic hydrocarbon compounds:
cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$) and methylcyclohexene ($C_7$); and
saturated polycyclic hydrocarbon compounds: norcarane (C7), norpinane ($C_7$), norbornane ($C_7$).

$C_{3-20}$ heterocyclyl: The term "$C_{3-20}$ heterocyclyl" as used herein, pertains to a monovalent moiety obtained by removing a hydrogen atom from a ring atom of a heterocyclic compound, which moiety has from 3 to 20 ring atoms, of which from 1 to 10 are ring heteroatoms. Preferably, each ring has from 3 to 7 ring atoms, of which from 1 to 4 are ring heteroatoms.

In this context, the prefixes (e.g. $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl", as used herein, pertains to a heterocyclyl group having 5 or 6 ring atoms.

Examples of monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of substituted monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

$C_{5-20}$ aryl: The term "$C_{5-20}$ aryl", as used herein, pertains to a monovalent moiety obtained by removing a hydrogen atom from an aromatic ring atom of an aromatic compound, which moiety has from 3 to 20 ring atoms. Preferably, each ring has from 5 to 7 ring atoms.

In this context, the prefixes (e.g. $C_{3-20}$, $C_{5-7}$, $C_{5-6}$, etc.) denote the number of ring atoms, or range of number of ring atoms, whether carbon atoms or heteroatoms. For example, the term "$C_{5-6}$ aryl" as used herein, pertains to an aryl group having 5 or 6 ring atoms.

The ring atoms may be all carbon atoms, as in "carboaryl groups". Examples of carboaryl groups include, but are not limited to, those derived from benzene (i.e. phenyl) ($C_6$), naphthalene ($C_{10}$), azulene ($C_{10}$), anthracene ($C_{14}$), phenanthrene ($C_{14}$), naphthacene ($C_{18}$), and pyrene ($C_{16}$)

Examples of aryl groups which comprise fused rings, at least one of which is an aromatic ring, include, but are not limited to, groups derived from indane (e.g. 2,3-dihydro-1H-indene) ($C_9$), indene ($C_9$), isoindene ($C_9$), tetraline (1,2,3,4-tetrahydronaphthalene ($C_{10}$), acenaphthene ($C_{12}$), fluorene ($C_{13}$), phenalene ($C_{13}$), acephenanthrene ($C_{15}$), and aceanthrene ($C_{16}$)

Alternatively, the ring atoms may include one or more heteroatoms, as in "heteroaryl groups". Examples of monocyclic heteroaryl groups include, but are not limited to, those derived from:

$N_1$: pyrrole (azole) ($C_5$), pyridine (azine) ($C_6$);

$O_1$: furan (oxole) ($C_5$);

$S_1$: thiophene (thiole) ($C_5$);

$N_1O_1$: oxazole ($C_5$), isoxazole ($C_5$), isoxazine ($C_6$);

$N_2O_1$: oxadiazole (furazan) ($C_5$);

$N_3O_1$: oxatriazole ($C_5$);

$N_1S_1$: thiazole ($C_5$), isothiazole ($C_5$);

$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);

$N_3$: triazole ($C_5$), triazine ($C_6$); and, $N_4$: tetrazole ($C_5$).

Examples of heteroaryl which comprise fused rings, include, but are not limited to:

$C_9$ (with 2 fused rings) derived from benzofuran ($O_1$), isobenzofuran ($O_1$), indole ($N_1$), isoindole ($N_1$), indolizine ($N_1$), indoline ($N_1$), isoindoline ($N_1$), purine ($N_4$) (e.g., adenine, guanine), benzimidazole ($N_2$), indazole ($N_2$), benzoxazole ($N_1O_1$), benzisoxazole ($N_1O_1$), benzodioxole ($O_2$), benzofurazan ($N_2O_1$), benzotriazole ($N_3$), benzothiofuran ($S_1$), benzothiazole ($N_1S_1$), benzothiadiazole ($N_2S$);

$C_{10}$ (with 2 fused rings) derived from chromene ($O_1$), isochromene ($O_1$), chroman ($O_1$), isochroman ($O_1$), benzodioxan ($O_2$), quinoline ($N_1$), isoquinoline ($N_1$), quinolizine ($N_1$), benzoxazine ($N_1O_1$), benzodiazine ($N_2$), pyridopyridine ($N_2$), quinoxaline ($N_2$), quinazoline ($N_2$), cinnoline ($N_2$), phthalazine ($N_2$), naphthyridine ($N_2$), pteridine ($N_4$);

$C_{11}$ (with 2 fused rings) derived from benzodiazepine ($N_2$);

$C_{13}$ (with 3 fused rings) derived from carbazole ($N_1$), dibenzofuran ($O_1$), dibenzothiophene ($S_1$), carboline ($N_2$), perimidine ($N_2$), pyridoindole ($N_2$); and, $C_{14}$ (with 3 fused rings) derived from acridine ($N_1$), xanthene ($O_1$), thioxanthene ($S_1$), oxanthrene ($O_2$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

The above groups, whether alone or part of another substituent, may themselves optionally be substituted with one or more groups selected from themselves and the additional substituents listed below.

Halo: —F, —Cl, —Br, and —I.

Hydroxy: —OH.

Ether: —OR, wherein R is an ether substituent, for example, a $C_{1-7}$ alkyl group (also referred to as a $C_{1-7}$ alkoxy group, discussed below), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$ alkyl group.

Alkoxy: —OR, wherein R is an alkyl group, for example, a $C_{1-7}$ alkyl group. Examples of $C_{1-7}$ alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

Acetal: —CH(OR$^1$)(OR$^2$), wherein R$^1$ and R$^2$ are independently acetal substituents, for example, a $C_{1-7}$ alkyl group, a $C_{3-20}$ heterocyclyl group, or a $C_{5-20}$ aryl group, preferably a $C_{1-7}$ alkyl group, or, in the case of a "cyclic" acetal group, R$^1$ and R$^2$, taken together with the two oxygen atoms to which they are attached, and the carbon atoms to which they are attached, form a heterocyclic ring having from 4 to 8 ring atoms. Examples of acetal groups include, but are not limited to, —CH(OMe)$_2$, —CH(OEt)$_2$, and —CH(OMe)(OEt).

Hemiacetal: —CH(OH)(OR$^1$), wherein R$^1$ is a hemiacetal substituent, for example, a $C_{1-7}$ alkyl group, a $C_{3-20}$ heterocyclyl group, or a $C_{5-20}$ aryl group, preferably a $C_{1-7}$ alkyl group. Examples of hemiacetal groups include, but are not limited to, —CH(OH)(OMe) and —CH(OH)(OEt).

Ketal: —CR(OR$^1$)(OR$^2$), where R$^1$ and R$^2$ are as defined for acetals, and R is a ketal substituent other than hydrogen, for example, a C$_{1-7}$ alkyl group, a C$_{3-20}$ heterocyclyl group, or a C$_{5-20}$ aryl group, preferably a C$_{1-7}$ alkyl group. Examples ketal groups include, but are not limited to, —C(Me) (OMe)$_2$, —C(Me) (OEt)$_2$, —C(Me) (OMe) (OEt), —C(Et) (OMe)$_2$, —C(Et) (OEt)$_2$, and —C(Et) (OMe) (OEt).

Hemiketal: —CR(OH) (OR$^1$), where R$^1$ is as defined for hemiacetals, and R is a hemiketal substituent other than hydrogen, for example, a C$_{1-7}$ alkyl group, a C$_{3-20}$ heterocyclyl group, or a C$_{5-20}$ aryl group, preferably a C$_{1-7}$ alkyl group. Examples of hemiacetal groups include, but are not limited to, —C(Me) (OH) (OMe), —C(Et) (OH) (OMe), —C(Me) (OH) (OEt), and —C (Et) (OH) (OEt).

Oxo (keto, -one): =O.

Thione (thioketone): =S.

Imino (imine): =NR, wherein R is an imino substituent, for example, hydrogen, C$_{1-7}$ alkyl group, a C$_{3-20}$ heterocyclyl group, or a C$_{5-20}$ aryl group, preferably hydrogen or a C$_{1-7}$ alkyl group. Examples of ester groups include, but are not limited to, =NH, =NMe, =NEt, and =NPh.

Formyl (carbaldehyde, carboxaldehyde): —C(=O) H.

Acyl (keto): —C(=O)R, wherein R is an acyl substituent, for example, a C$_{1-7}$ alkyl group (also referred to as C$_{1-7}$ alkylacyl or C$_{1-7}$ alkanoyl), a C$_{3-20}$ heterocyclyl group (also referred to as C$_{3-20}$ heterocyclylacyl), or a C$_{5-20}$ aryl group (also referred to as C$_{5-20}$ arylacyl), preferably a C$_{1-7}$ alkyl group. Examples of acyl groups include, but are not limited to, —C(=O) CH$_3$ (acetyl), —C (=O) CH$_2$CH$_3$ (propionyl), —C(=O)C(CH$_3$)$_3$ (t-butyryl), and —C(=O)Ph (benzoyl, phenone).

Carboxy (carboxylic acid): —C(=O)OH.

Thiocarboxy (thiocarboxylic acid): —C(=S)SH.

Thiolocarboxy (thiolocarboxylic acid): —C(=O)SH.

Thionocarboxy (thionocarboxylic acid): —C(=S)OH.

Imidic acid: —C(=NH)OH.

Hydroxamic acid: —C(=NOH)OH.

Ester (carboxylate, carboxylic acid ester, oxycarbonyl): —C(=O)OR, wherein R is an ester substituent, for example, a C$_{1-7}$ alkyl group, a C$_{3-20}$ heterocyclyl group, or a C$_{5-20}$ aryl group, preferably a C$_{1-7}$ alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a C$_{1-7}$ alkyl group, a C$_{3-20}$ heterocyclyl group, or a C$_{5-20}$ aryl group, preferably a C$_{1-7}$ alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Oxycarboyloxy: —OC(=O)OR, wherein R is an ester substituent, for example, a C$_{1-7}$ alkyl group, a C$_{3-20}$ heterocyclyl group, or a C$_{5-20}$ aryl group, preferably a C$_{1-7}$ alkyl group. Examples of ester groups include, but are not limited to, —OC(=O)OCH$_3$, —OC(=O)OCH$_2$CH$_3$, —OC(=O)OC(CH$_3$)$_3$, and —OC(=O)OPh.

Amino: —NR$^1$R$^2$, wherein R$^1$ and R$^2$ are independently amino substituents, for example, hydrogen, a C$_{1-7}$ alkyl group (also referred to as C$_{1-7}$ alkylamino or di—C$_{1-7}$ alkylamino), a C$_{3-20}$ heterocyclyl group, or a C$_{5-20}$aryl group, preferably H or a C$_{1-7}$ alkyl group, or, in the case of a "cyclic" amino group, R$^1$ and R$^2$, taken together with the nitrogen atom to which they are attached, form a heterocyclic ring having from 4 to 8 ring atoms. Amino groups may be primary (—NH$_2$), secondary (—NHR$^1$), or tertiary (—NHR$^1$R$^2$), and in cationic form, may be quaternary (—$^+$NR$^1$R$^2$R$^3$). Examples of amino groups include, but are not limited to, —NH$_2$, —NHCH$_3$, —NHC(CH$_3$)$_2$, —N(CH$_2$CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Thioamido (thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(=S)NHCH$_3$, —C(=S)N(CH$_3$)$_2$, and —C(=S)NHCH$_2$CH$_3$.

Acylamido (acylamino): —NR$^1$C(=O)R$^2$, wherein R$^1$ is an amide substituent, for example, hydrogen, a C$^{1-7}$ alkyl group, a C$_{3-20}$ heterocyclyl group, or a C$_{5-20}$ aryl group, preferably hydrogen or a C$_{1-7}$ alkyl group, and R$^2$ is an acyl substituent, for example, a C$_{1-7}$ alkyl group, a C$_{3-20}$ heterocyclyl group, or a C$_{5-20}$ aryl group, preferably hydrogen or a C$_{1-7}$ alkyl group. Examples of acylamide groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, succinimidyl, maleimidyl, and phthalimidyl:

succinimidyl        maleimidyl        phthalimidyl

Aminocarbonyloxy: —OC(=O)NR$^1$R$^2$, wherein R$^1$ and R$^2$ are independently amino substituents, as defined for amino groups. Examples of aminocarbonyloxy groups include, but are not limited to, —OC(=O)NH$_2$, —OC(=O)NHMe, —OC(=O)NMe$_2$, and —OC(=O)NEt$_2$.

Ureido: —N(R$^1$)CONR$^2$R$^3$ wherein R$^2$ and R$^3$ are independently amino substituents, as defined for amino groups, and R$^1$ is a ureido substituent, for example, hydrogen, a C$_{1-7}$ alkyl group, a C$_{3-20}$ heterocyclyl group, or a C$_{5-20}$ aryl group, preferably hydrogen or a C$_{1-7}$ alkyl group. Examples of ureido groups include, but are not limited to, —NHCONH$_2$, —NHCONHMe, —NHCONHEt, —NHCONMe$_2$, —NHCONEt$_2$, —NMeCONH$_2$, —NMeCONHMe, —NMeCONHEt, —NMeCONMe$_2$, and —NMeCONEt$_2$.

Guanidino: —NH—C(=NH)NH$_2$.

Tetrazolyl: a five membered aromatic ring having four nitrogen atoms and one carbon atom, Imino: =NR, wherein R is an imino substituent, for example, for example, hydrogen, a C$_{1-7}$ alkyl group, a C$_{3-20}$ heterocyclyl group, or a C$_{5-20}$ aryl group, preferably H or a $C_{1-7}$ alkyl group. Examples of imino groups include, but are not limited to, =NH, =NMe, and =NEt.

Amidine (amidino): —C(=NR)NR$_2$, wherein each R is an amidine substituent, for example, hydrogen, a $C_{1-7}$ alkyl group, a $C_{3-20}$ heterocyclyl group, or a $C_{5-20}$ aryl group, preferably H or a $C_{1-7}$ alkyl group. Examples of amidine groups include, but are not limited to, —C(=NH)NH$_2$, —C(=NH)NMe$_2$, and —C(=NMe)NMe$_2$.

Nitro: —NO$_2$.
Nitroso: —NO.
Azido: —N$_3$.
Cyano (nitrile, carbonitrile): —CN.
Isocyano: —NC.
Cyanato: —OCN.
Isocyanato: —NCO.
Thiocyano (thiocyanato): —SCN.
Isothiocyano (isothiocyanato): —NCS.
Sulfhydryl (thiol, mercapto): —SH.
Thioether (sulfide): —SR, wherein R is a thioether substituent, for example, a $C_{1-7}$ alkyl group (also referred to as a $C_{1-7}$alkylthio group), a $C_{3-20}$ heterocyclyl group, or a $C_{5-20}$ aryl group, preferably a $C_{1-7}$ alkyl group. Examples of $C_{1-7}$ alkylthio groups include, but are not limited to, —SCH$_3$ and —SCH$_2$CH$_3$.

Disulfide: —SS—R, wherein R is a disulfide substituent, for example, a $C_{1-7}$ alkyl group, a $C_{3-20}$ heterocyclyl group, or a $C_{5-20}$ aryl group, preferably a $C_{1-7}$ alkyl group (also referred to herein as $C_{1-7}$ alkyl disulfide). Examples of $C_{1-7}$ alkyl disulfide groups include, but are not limited to, —SSCH$_3$ and —SSCH$_2$CH$_3$.

Sulfine (sulfinyl, sulfoxide): —S(=O)R, wherein R is a sulfine substituent, for example, a $C_{1-7}$ alkyl group, a $C_{3-20}$ heterocyclyl group, or a $C_{5-20}$ aryl group, preferably a $C_{1-7}$ alkyl group. Examples of sulfine groups include, but are not limited to, —S(=O)CH$_3$ and —S(=O)CH$_2$CH$_3$.

Sulfone (sulfonyl): —S(=O)$_2$R, wherein R is a sulfone substituent, for example, a $C_{1-7}$ alkyl group, a $C_{3-20}$ heterocyclyl group, or a $C_{5-20}$ aryl group, preferably a $C_{1-7}$ alkyl group, including, for example, a fluorinated or perfluorinated $C_{1-7}$ alkyl group. Examples of sulfone groups include, but are not limited to, —S(=O)$_2$CH$_3$ (methanesulfonyl, mesyl), —S(=O)$_2$CF$_3$ (triflyl), —S(=O)$_2$CH$_2$CH$_3$ (esyl), —S(=O)$_2$C$_4$Fg (nonaflyl), —S(=O)$_2$CH$_2$CF$_3$ (tresyl), —S(=O)$_2$CH$_2$CH$_2$NH$_2$ (tauryl), —S(=O)$_2$Ph (phenylsulfonyl, besyl), 4-methylphenylsulfonyl (tosyl), 4-chlorophenylsulfonyl (closyl), 4-bromophenylsulfonyl (brosyl), 4-nitrophenyl (nosyl), 2-naphthalenesulfonate (napsyl), and 5-dimethylamino-naphthalen-1-ylsulfonate (dansyl).

Sulfinic acid (sulfino): —S(=O)OH, —SO$_2$H.
Sulfonic acid (sulfo): —S(=O)$_2$OH, —SO$_3$H.
Sulfinate (sulfinic acid ester): —S(=O)OR; wherein R is a sulfinate substituent, for example, a $C_{1-7}$ alkyl group, a $C_{3-20}$ heterocyclyl group, or a $C_{5-20}$ aryl group, preferably a $C_{1-7}$ alkyl group. Examples of sulfinate groups include, but are not limited to, —S(=O)OCH$_3$ (methoxysulfinyl; methyl sulfinate) and —S(=O)OCH$_2$CH$_3$ (ethoxysulfinyl; ethyl sulfinate).

Sulfonate (sulfonic acid ester): —S(=O)$_2$OR, wherein R is a sulfonate substituent, for example, a $C_{1-7}$ alkyl group, a $C_{3-20}$ heterocyclyl group, or a $C_{5-20}$ aryl group, preferably a $C_{1-7}$ alkyl group. Examples of sulfonate groups include, but are not limited to, —S(=O)$_2$OCH$_3$ (methoxysulfonyl; methyl sulfonate) and —S(=O)$_2$OCH$_2$CH$_3$ (ethoxysulfonyl; ethyl sulfonate).

Sulfinyloxy: —OS(=O)R, wherein R is a sulfinyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfinyloxy groups include, but are not limited to, —OS(=O)CH$_3$ and —OS(=O)CH$_2$CH$_3$.

Sulfonyloxy: —OS(=O)$_2$R, wherein R is a sulfonyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfonyloxy groups include, but are not limited to, —OS(=O)$_2$CH$_3$ (mesylate) and —OS(=O)$_2$CH$_2$CH$_3$ (esylate).

Sulfate: —OS(=O)$_2$OR; wherein R is a sulfate substituent, for example, a $C_{1-7}$ alkyl group, a $C_{3-20}$heterocyclyl group, or a $C_{5-20}$ aryl group, preferably a $C_{1-7}$ alkyl group. Examples of sulfate groups include, but are not limited to, —OS(=O)$_2$OCH$_3$ and —SO(=O)$_2$OCH$_2$CH$_3$.

Sulfamyl (sulfamoyl; sulfinic acid amide; sulfinamide): —S(=O)NR$^1$R$^2$, wherein R$^1$ and R$^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamido (sulfinamoyl; sulfonic acid amide; sulfonamide): —S(=O)$_2$NR$^1$R$^2$, wherein R$^1$ and R$^2$ are independently amino substituents, as defined for amino groups. Examples of sulfonamido groups include, but are not limited to, —S(=O)$_2$NH$_2$, —S(=O)$_2$NH(CH$_3$), —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

Sulfamino: —NR$^1$S(=O)$_2$OH, wherein R$^1$ is an amino substituent, as defined for amino groups. Examples of sulfamino groups include, but are not limited to, —NHS(=O)$_2$OH and —N(CH$_3$)S(=O)$_2$OH.

Sulfonamino: —NR$^1$S(=O)$_2$R, wherein R$^1$ is an amino substituent, as defined for amino groups, and R is a sulfonamino substituent; for example, a $C_{1-7}$ alkyl group, a $C_{3-20}$ heterocyclyl group, or a $C_{5-20}$ aryl group, preferably a $C_{1-7}$ alkyl group. Examples of sulfonamino groups include, but are not limited to, —NHS(=O)$_2$CH$_3$ and —N(CH$_3$)S(=O)$_2$C$_6$H$_5$.

Sulfinamino: —NR$^1$S(=O)R, wherein R$^1$ is an amino substituent, as defined for amino groups, and R is a sulfinamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfinamino groups include, but are not limited to, —NHS(=O)$_2$CH$_3$ and —N(CH$_3$)S(=O)C$_6$H$_5$.

Phosphino (phosphine): —PR$_2$, wherein R is a phosphino substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphino groups include, but are not limited to, —PH$_2$, —P(CH$_3$)$_2$, —P(CH$_2$CH$_3$)$_2$, —P(t-Bu)$_2$, and —P(Ph)$_2$.

Phospho: —P(=O)$_2$.

Phosphinyl (phosphine oxide): —P(=O)R$_2$, wherein R is a phosphinyl substituent, for example, a $C_{1-7}$ alkyl group, a $C_{3-20}$ heterocyclyl group, or a $C_{5-20}$ aryl group, preferably a $C_{1-7}$ alkyl group or a $C_{5-20}$ aryl group. Examples of phosphinyl groups include, but are not limited to, —P(=O)(CH$_3$)$_2$, —P(=O)(CH$_2$CH$_3$)$_2$, —P(=O)(t-Bu)$_2$, and —P(=O)(Ph)$_2$.

Phosphonic acid (phosphono): —P(=O)(OH)$_2$.

Phosphonate (phosphono ester): —P(=O)(OR)$_2$, where R is a phosphonate substituent, for example, —H, a $C_{1-7}$ alkyl group, a $C_{3-20}$ heterocyclyl group, or a $C_{5-20}$aryl group, preferably —H, a $C_{1-7}$ alkyl group, or a $C_{5-20}$ aryl group. Examples of phosphonate groups include, but are not limited to, —P(=O)(OCH$_3$)$_2$, —P(=O)(OCH$_2$CH$_3$)$_2$, —P(=O)(O-t-Bu)$_2$, and —OP(=O)(OPh)$_2$.

Phosphoric acid (phosphonooxy): —OP(=O)(OH)$_2$.

Phosphate (phosphonooxy ester): —OP(=O) (OR)$_2$, where R is a phosphate substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphate groups include, but are not limited to, —OP(=O)(OCH$_3$)$_2$, —OP(=O)(OCH$_2$CH$_3$)$_2$, —OP(=O)(O-t-Bu)$_2$, and —OP(=O) (OPh)$_2$.

Phosphorous acid: —OP(OH)$_2$.

Phosphite: —OP(OR)$_2$, where R is a phosphite substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphite groups include, but are not limited to, —OP(OCH$_3$)$_2$, —OP(OCH$_2$CH$_3$)$_2$, —OP (O-t-Bu)$_2$, and —OP(OPh)$_2$.

Phosphoramidite: —OP(OR$^1$) —NR$^2_2$, where R$^1$ and R$^2$ are phosphoramidite substituents, for example, —H, a (optionally substituted) C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphoramidite groups include, but are not limited to, —OP(OCH$_2$CH$_3$)—N(CH$_3$)$^2$, —OP(OCH$_2$CH$_3$)—N(i-Pr)$_2$, and —OP(OCH$_2$CH$_2$CN)—N(i-Pr)$_2$.

Phosphoramidate: —OP(=O) (OR$^1$)—NR$^2_2$, where R$^1$ and R$^2$ are phosphoramidate substituents, for example, —H, a (optionally substituted) C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphoramidate groups include, but are not limited to, —OP(=O)(OCH$_2$CH$_3$)—N(CH$_3$)$_2$, —OP (=O) (OCH$_2$CH$_3$) —N(i-Pr)$_2$, and —OP(=O) (OCH$_2$CH$_2$CN)—N(i-Pr)$_2$.

Alkylene

C$_{3-12}$ alkylene: The term "C$_{3-12}$ alkylene", as used herein, pertains to a bidentate moiety obtained by removing two hydrogen atoms, either both from the same carbon atom, or one from each of two different carbon atoms, of a hydrocarbon compound having from 3 to 12 carbon atoms (unless otherwise specified), which may be aliphatic or alicyclic, and which may be saturated, partially unsaturated, or fully unsaturated. Thus, the term "alkylene" includes the sub-classes alkenylene, alkynylene, cycloalkyiene, etc., discussed below.

Examples of linear saturated C$_{3-12}$ alkylene groups include, but are not limited to, —(CH$_2$)$_n$— where n is an integer from 3 to 12, for example, —CH$_2$CH$_2$CH$_2$— (propylene), —CH$_2$CH$_2$CH$_2$CH$_2$— (butylene), —CH$_2$CH$_2$CH$_2$CH$_2$CH$_2$— (pentylene) and —CH$_2$CH$_2$CH$_2$CH$_2$CH$_2$CH$_2$CH$_2$— (heptylene).

Examples of branched saturated C$_{3-12}$ alkylene groups include, but are not limited to, —CH (CH$_3$) CH$_2$—, —CH (CH$_3$) CH$_2$CH$_2$—, —CH (CH$_3$) CH$_2$CH$_2$CH$_2$—, —CH$_2$CH (CH$_3$) CH$_2$—, —CH$_2$CH (CH$_3$) CH$_2$CH$_2$—, —CH (CH$_2$CH$_3$)—, —CH (CH$_2$CH$_3$) CH$_2$—, and —CH$_2$CH (CH$_2$CH$_3$) CH$_2$—.

Examples of linear partially unsaturated C$_{3-12}$ alkylene groups (C$_{3-12}$ alkenylene, and alkynylene groups) include, but are not limited to, —CH=CH—CH$_2$—, —CH$_2$—CH=CH$_2$—, —CH=CH—CH$_2$—CH$_2$—, —CH=CH—CH$_2$—CH$_2$—CH$_2$—, —CH=CH—CH$_2$CH=CH—, —CH=CH—, —CH=CH—CH=CH—CH$_2$—, —CH=CH—CH=CH—CH$_2$—CH$_2$—, —CH=CH—CH$_2$—CH=CH—, —CH=CH—CH$_2$—CH$_2$—CH=CH—, and —CH$_2$—C≡C—CH$_2$—.

Examples of branched partially unsaturated C$_{3-12}$ alkylene groups (C$_{3-12}$ alkenylene and alkynylene groups) include, but are not limited to, —C(CH$_3$)=CH—, —C(CH$_3$)=CH—CH$_2$—, —CH=CH—CH(CH$_3$)— and —C≡C—CH(CH$_3$)—.

Examples of alicyclic saturated C$_{3-12}$ alkylene groups (C$_{3-12}$ cycloalkylenes) include, but are not limited to, cyclopentylene (e.g. cyclopent-1,3-ylene), and cyclohexylene (e.g. cyclohex-1,4-ylene).

Examples of alicyclic partially unsaturated C$_{3-12}$ alkylene groups (C$_{3-12}$ cycloalkylenes) include, but are not limited to, cyclopentenylene (e.g. 4-cyclopenten-1,3-ylene), cyclohexenylene (e.g. 2-cyclohexen-1,4-ylene; 3-cyclohexen-1,2-ylene; 2,5-cyclohexadien-1,4-ylene).

Includes Other Forms

Unless otherwise specified, included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms.

Isomers, Salts, Solvates, Protected Forms, and Prodrugs

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r- forms; endo- and exo-forms; R-, S-, and meso-forms; D- and L-forms; d- and 1-forms; (+) and (−) forms; keto-, enol-, and enolate-forms; syn- and anti-forms; synclinal-and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g. C$_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

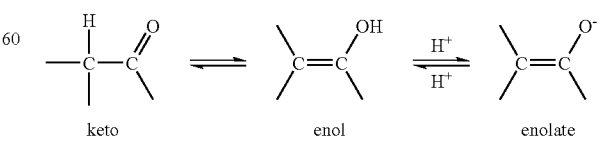

keto          enol          enolate

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below.

It may be convenient or desirable to prepare, purify, and/or handle a corresponding salt of the active compound, for example, a pharmaceutically-acceptable salt. Examples of pharmaceutically acceptable salts are discussed in Berge, et al., *J. Pharm. Sci.*, 66, 1-19 (1977).

For example, if the compound is anionic, or has a functional group which may be anionic (e.g. —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e. NH$_4^+$) and substituted ammonium ions (e.g. NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g. —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

Solvates of particular relevance to the present invention are those where the solvent adds across the imine bond of the PBD moiety, which is illustrated below where the solvent is water or an alcohol (R$^A$OH, where R$^A$ is an ether substituent as described above):

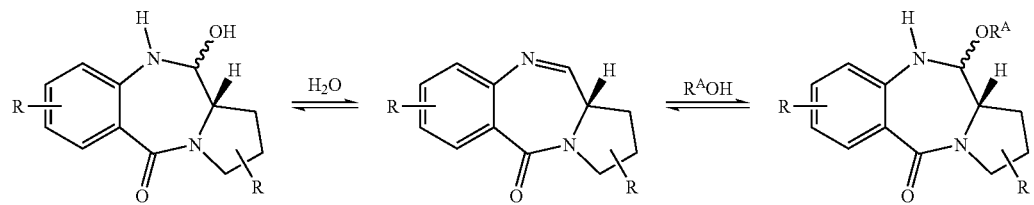

These forms can be called the carbinolamine and carbinolamine ether forms of the PBD. The balance of these equilibria depend on the conditions in which the compounds are found, as well as the nature of the moiety itself.

In general any nuceleophilic solvent is capable of forming such solvates as illustrated above for hydoxylic solvents. Other nuceleophilic solvents include thiols and amines.

It may be convenient or desirable to prepare, purify, and/or handle the active compound in a chemically protected form. The term "chemically protected form" is used herein in the conventional chemical sense and pertains to a compound in which one or more reactive functional groups are protected from undesirable chemical reactions under specified conditions (e.g. pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, "Protective Groups in Organic Synthesis" (Green, T. and Wuts, P.; 3rd Edition; John Wiley and Sons, 1999).

A wide variety of such "protecting", "blocking", or "masking" methods are widely used and well known in organic synthesis. For example, a compound which has two non-equivalent reactive functional groups, both of which would be reactive under specified conditions, may be derivatized to render one of the functional groups "protected", and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)CH$_3$, —OAc).

For example, an aldehyde or ketone group may be protected as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH—Cbz); as a t-butoxy amide (—NHCO—OC(CH$_3$)$_3$, —NH—-Boc);a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH—Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases (e.g., cyclic amines), as a nitroxide radical (>N—O).

For example, a carboxylic acid group may be protected as an ester for example, as: an C$_{1-7}$ alkyl ester (e.g. a methyl ester; a t-butyl ester); a C$_{1-7}$ haloalkyl ester (e.g. a C$_{1-7}$ trihaloalkyl ester); a triC$_{1-7}$ alkylsilyl-C$_{1-7}$ alkyl ester; or a C$_{5-20}$ aryl-C$_{1-7}$ alkyl ester (e.g. a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

It may be convenient or desirable to prepare, purify, and/or handle the active compound in the form of a prodrug. The term "prodrug", as used herein, pertains to a compound which, when metabolised (e.g. in vivo), yields the desired active compound.

Typically, the prodrug is inactive, or less active than the active compound, but may provide advantageous handling, administration, or metabolic properties.

For example, some prodrugs are esters of the active compound (e.g. a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

In particular, prodrugs of pyrrolobenzodiazepines are described in WO 00/12507, which is incorporated herein by reference. In these prodrugs a nitrogen protecting group which can be removed in vivo (e.g. enzymatically, using light) is bound to the nitrogen of the imine group, with the carbon of the imine group bearing a hydroxy, ester or thioester group. Examples of this form of protection include:

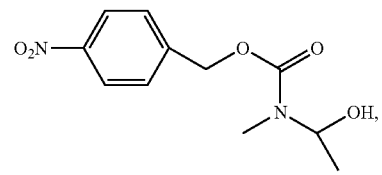

which is nitroreductase labile (e.g. using ADEPT/GDEPT);

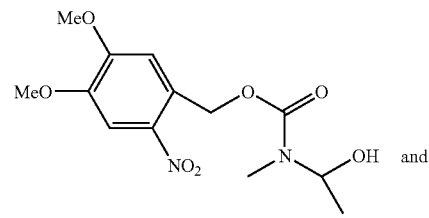

and

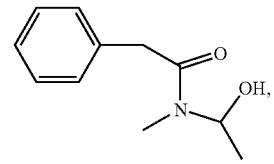

which are photolabile; and

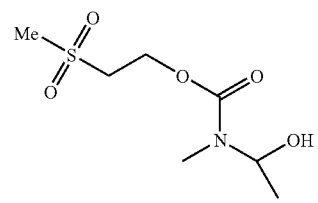

which is glutathione labile (e.g. using NPEPT).

General Synthetic Routes

A key intermediate in the synthesis of the compounds of the present invention is the following compound, an enol triflate, of formula (A):

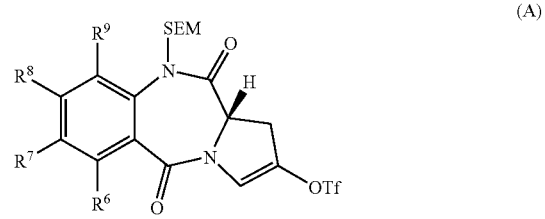

(A)

wherein the groups R$^6$ to R$^9$ are as for the final product, SEM represents a trimethyl silyl ethoxy methyl group, and OTf represents the group OSO$_2$CF$_3$. The synthesis of this compound is described in detail in WO 00/12508, which is incorporated herein by reference. In particular, reference is made to scheme 7 on page 24, where the above compound is designated as intermediate P. The SEM protecting group can be replaced by other suitable nitrogen protecting groups.

The route from this compound to the desired final product is illustrated in scheme 1.

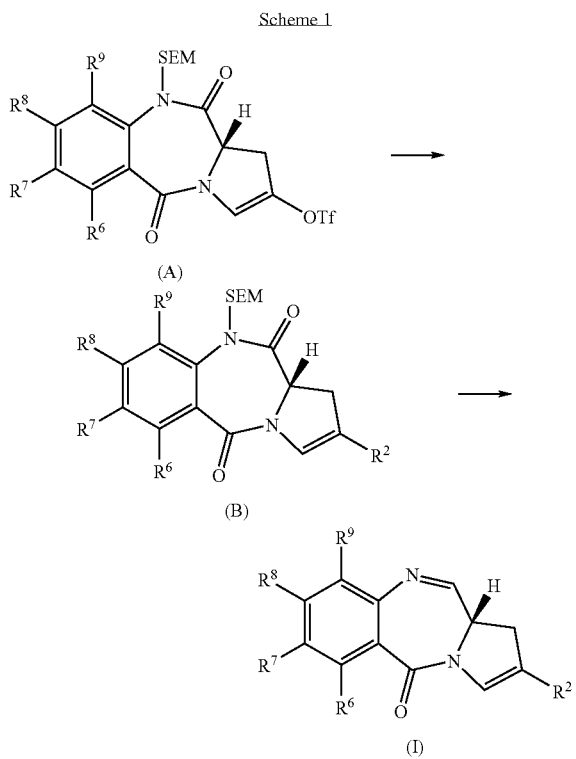

The key enol triflate intermediate (A) can be converted to the appropriate SEM protected dilactam (B) by use of a Suzuki coupling reaction, i.e. palladium catalysed cross coupling of the enol triflate (A) with the appropriate arylboron derivative.

The SEM protected dilactam (B) can then by converted to the desired final compound of formula (I) by reduction, which leads to a protected carbinolamine intermediate, which can then be treated to remove the SEM protecting group. The reduction of the dilactam (B) can be accomplished by, for example, sodium tetraborohydride, whilst a suitable means for removing the SEM protecting group is treatment with silica gel.

This synthesis route is equally applicable to the synthesis of dimers.

Further Uses

The present invention also provides compounds as described in the first aspect of the invention which regulate (e.g. inhibit) cell proliferation. Thus, the present invention also provides methods of regulating (e.g. inhibiting) cell proliferation, in vitro or in vivo, comprising contacting a cell with an effective amount of a compound of the first aspect of the invention.

In particular, this inhibition may be of certain cell lines as disclosed in the examples.

One of ordinary skill in the art is readily able to determine whether or not a candidate compound regulate (e.g. inhibit) cell proliferation. For example, assays which may conveniently be used to assess the activity offered by a particular compound are described in the examples below.

For example, a sample of cells (e.g. from a tumour) may be grown in vitro and a test compound brought into contact with said cells, and the effect of the compound on those cells observed. As an example of "effect" the morphological status of the cells (e.g. alive or dead, etc.) may be determined. Where the test compound is found to exert an influence on the cells, this may be used as a prognostic or diagnostic marker of the efficacy of the compound in methods of treating a patient carrying cells of the same cellular type.

Methods of Treatment

As described above, the second aspect of the invention provide the use of a compound of the first aspect of the invention in a method of therapy. Also provided is a method of treatment, comprising administering to a subject in need of treatment a therapeutically-effective amount of a compound of the first aspect of the invention, preferably in the form of a pharmaceutical composition, which is the third aspect of the present invention. The term "therapeutically effective amount" is an amount sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

A compound may be administered alone or in combination with other treatments, either simultaneously or sequentially dependent upon the condition to be treated. Examples of treatments and therapies include, but are not limited to, chemotherapy (the administration of active agents, including, e.g. drugs; surgery; and radiation therapy.

Pharmaceutical compositions according to the present invention, and for use in accordance with the present invention, may comprise, in addition to the active ingredient, i.e. a compound of formula I, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous, or intravenous.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such a gelatin.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Preferences

The following preferences may apply to all aspects of the invention as described above, or may relate to a single aspect. The preferences may be combined together in any combination.

$R^6$ to $R^9$

If the compound is a dimer, it is preferred that the dimer bridge is of formula —O—$(CH_2)_n$—O—, where n is from 3 to 12, and more preferably 3 to 7.

$R^9$ is preferably H.

$R^6$ is preferably selected from H, OH, OR, SH, $NH_2$, nitro and halo, and is more preferably H or halo, and most preferably is H.

$R^7$ and $R^8$ (when the compound is not a dimer) are preferably independently selected from H, OH, OR, SH, SR, $NH_2$, NHR, NHRR', and halo, and more preferably independently selected from H, OH and OR, where R is preferably selected from optionally substituted $C_{1-7}$ alkyl, $C_{3-10}$ heterocyclyl and $C_{5-10}$ aryl groups. Particularly preferred substituents at the 7- and 8-positions are OMe and $OCH_2Ph$.

$R^2$

In one set of embodiments $R^2$ is an optionally substituted napthyl group. Preferred substituents include: halo, more particularly chloro and fluoro; $C_{1-7}$ alkyl groups, more particularly $C_{1-4}$ alkyl groups, e.g. methyl and t-butyl; ether groups, more particularly $C_{1-4}$ alkoxy groups, e.g. methoxy and benzyloxy; $C_{5-20}$ aryl groups, particularly phenyl.

The napthyl group may be linked to the main PBD moiety at any position on its ring system. For example, if the napthyl is unsubstituted, then the group may either be napth-1-yl or napth-2-yl, with napth-2-yl being preferred.

Especially preferred napthyl groups include: napth-2-yl, 6-methoxy-napth-2-yl, 6-ethoxy-napth-2-yl and fluoro and/or chloro substituted napthyl groups, with single substituted fluoro or chloro napth-2-yls being most preferred.

The optional substituents may also be at any ring position. It is preferred that there is not one substituent group either side of the bond to the main PBD moiety.

In one set of embodiments $R^2$ is an optionally substituted thiophenyl group. Preferred substituents include: halo, more particularly chloro and fluoro; $C_{1-7}$ alkyl groups, more particularly $C_{1-4}$ alkyl groups, e.g. methyl and t-butyl; ether groups, more particularly $C_{1-4}$ alkoxy groups, e.g. methoxy and benzyloxy; $C_{5-20}$ aryl groups, particularly phenyl.

The thiophenyl group may be linked to the main PBD moiety at any available position on its ring system. For example, if the thiophenyl is unsubstituted, then the group may either be thiophen-2-yl or thiophen-3-yl, with thiophen-2-yl being preferred.

Especially preferred thiophenyl groups include: thiophen-2-yl, 5-chloro-thiophen-2-yl and 5-methyl-thiophen-2-yl.

The optional substituents may also be at any ring position. If the thiophenyl group is thiophen-3-yl, then it is preferred that there is not one substituent group either side of the bond to the main PBD moiety.

In one set of embodiments $R^2$ is an optionally substituted furanyl group. Preferred substituents include: halo, more particularly chloro and fluoro; $C_{1-7}$ alkyl groups, more particularly $C_{1-4}$ alkyl groups, e.g. methyl and t-butyl; ether groups, more particularly $C_{1-4}$ alkoxy groups, e.g. methoxy and benzyloxy; $C_{5-20}$ aryl groups, particularly phenyl.

The furanyl group may be linked to the main PBD moiety at any available position on its ring system. For example, if the furanyl is unsubstituted, then the group may either be furan-2-yl or furan-3-yl, with furan-2-yl being preferred.

Especially preferred furanyl groups include: furan-2-yl, 5-chloro-furan-2-yl and 5-methyl-furan-2-yl.

The optional substituents may also be at any ring position. If the furanyl group is furan-3-yl, then it is preferred that there is not one substituent group either side of the bond to the main PBD moiety.

In another set of embodiments $R^2$ is a phenyl group substituted by an ethyl or propyl group, preferably an ethyl or n-propyl group and more preferably an ethyl group. These groups are preferably in the ortho (2-) or para (4-) positions, with ortho (2-) being more preferred.

Thus an especially preferred $R^2$ group of this type is 4-ethylphenyl.

In another set of embodiments $R^2$ is a phenyl group substituted by one or more chloro or fluoro groups. If there is only one substituent group this is preferably in the ortho (2-) or para (4-) positions, and more preferably in the para (4-) position. If there are two or more substituents, in general the ortho and para positions are the preferred substituent sites. However, it is preferred that there are not two chloro substituents at the 2and 6-positions. It is also preferred that all the substituents are either fluoro or chloro.

Especially preferred $R^2$ groups of this type are: 4-chlorophenyl; 4-fluorophenyl; 2-chlorophenyl; 2-fluorophenyl; 2,6-difluorophenyl; and 3,4-dichlorophenyl.

The following compounds are particularly preferred:
(11aS)-1,11a-dihydro-7,8-dimethoxy-2-(2-napthyl)-5H-pyrrolo[2,1-c][1,4]benzodiazepin-5-one (11)
(11aS)-1,11a-dihydro-7,8-dimethoxy-2-(4-tert-butylbenzene)-5H -pyrrolo[2,1-c][1,4]bezodiazepin-5-one (13)
(11aS)-1,11a-dihydro-7,8-dimethoxy-2-(4-chlorobenzene)-5H-pyrrolo[2,1-c][1,4]benzodiazepin-5-one (15)
(11aS)-1,11a-dihydro-7,8-dimethoxy-2-(4-fluorobenzene)-5H-pyrrolo[2,1-c][1,4]benzodiazepin-5-one (17)
(11aS)-1,11a-dihydro-7,8-dimethoxy-2-(2-methylbenzene)-5H-pyrrolo[2,1-c][1,4]benzodiazepin-5-one (19)
(11aS)-1,11a-dihydro-7,8-dimethoxy-2-(4-ethylbenzene)-5H-pyrrolo[2,1-c][1,4]benzodiazepin-5-one (21)
(11aS)-1,11a-dihydro-7,8-dimethoxy-2-(2-thiophenyl)-5H-pyrrolo[2,1-c][1,4]benzodiazepin-5-one (23)
(11aS)-1,11a-dihydro-7,8-dimethoxy-2-(2-furan)-5H-pyrrolo[2,1-c][1,4]benzodiazepin-5-one (25)
(11aS)-1,11a-dihydro-7,8-dimethoxy-2-(2,6-dimethylbenzene)-5H-pyrrolo[2,1-c][1,4]benzodiazepin-5-one (27)

The compounds of the first aspect of the invention are preferably used in treating, and in manufacturing medicaments to treat, cancers, and in particular breast, renal and lung cancers and for inhibiting the growth of breast, renal and lung cancer cell lines.

In particular, compounds where $R^2$ is an optionally substitued napthyl or thiophenyl group, are preferably used in treating, and in manufacturing medicaments to treat, lung, breast and renal cancer and melanomas, and more preferably breast cancer.

Compounds where $R^2$ is a phenyl group with an ethyl or propyl substituent are preferably used in treating, and in manufacturing medicaments to treat, lung, breast and renal cancer and melanomas.

Compounds where $R^2$ is a phenyl group with one or more fluoro substituents (preferably a 4-fluoro substituent) are preferably used in treating, and in manufacturing medicaments to treat, renal cancer.

Compounds where $R^2$ is a phenyl group with a 4-t-butyl substituent, one or more chloro substituents (preferably a 4-chloro substituent), or a 2-methyl substituent are preferably used in treating, and in manufacturing medicaments to treat, breast cancer. Compounds where $R^2$ is a phenyl group with a 4-t-butyl substituent are also preferably used in treating, and in manufacturing medicaments to treat, melanomas and renal cancer.

Compounds where $R^2$ is a phenyl group with a 2-methyl substituent are preferably used in treating, and in manufacturing medicaments to treat, renal cancer.

Compounds where $R^2$ is a phenyl group with 2,6-dimethyl substituents are preferably used in treating, and in manufacturing medicaments to treat, renal cancer.

EXAMPLES

General Experimental Methods

Melting points (mp) were determined on a Gallenkamp P1384 digital melting point apparatus and are uncorrected. Infrared (IR) spectra were recorded using a Perkin-Elmer 297 spectrophotometer. $^1$H— and $^{13}$C— NMR spectra were recorded on either a Jeol GSX 270 MHZ FT-NMR spectrometer or a Brucker AMX-250 MHz NMR spectrometer operating at 20° C. +/−1° C. Chemical shifts are reported in parts per million (δ) downfield from tetramethylsilane (TMS). Spin multiplicities are described as: s (singlet), bs (broad singlet), d (doublet), dd (doublet of doublets), t (triplet), q (quartet), p (pentuplet) or m (multiplet). Mass spectra (MS) were recorded using a Jeol JMS-DX 303 GC Mass Spectrometer (EI mode: 70 eV, source 117-147° C.). Accurate molecular masses (HRMS) were determined by peak matching using perfluorokerosene (PFK) as an internal mass marker, and FAB mass spectra were obtained from a glycerol/thioglycerol/trifluoroacetic acid (1:1:0.1) matrix with a source temperature of 180° C. Optical rotations at the Na-D line were obtained at ambient temperature using a Perkin-Elmer 141 Polarimeter. Analytical results were generally within +/−0.2% of the theoretical values. Flash chromatography was performed using Aldrich flash chromatography Silica Gel-60 (E. Merck, 230-400 mesh). Automated flash chromatography was carried out on a Jones Flashmaster II. Thin-layer chromatography (TLC) was performed using GF$_{254}$ silica gel (with fluorescent indicator) on glass plates. All solvents and reagents, unless otherwise stated, were supplied by the Aldrich Chemical Company Ltd. and were used as supplied without further purification. Anhydrous solvents were prepared by distillation under a dry nitrogen atmosphere in the presence of an appropriate drying agent, and were stored over 4 Å molecular sieves or sodium wire. Petroleum ether refers to the fraction boiling at 40-60° C.

Synthesis of Key Intermediate

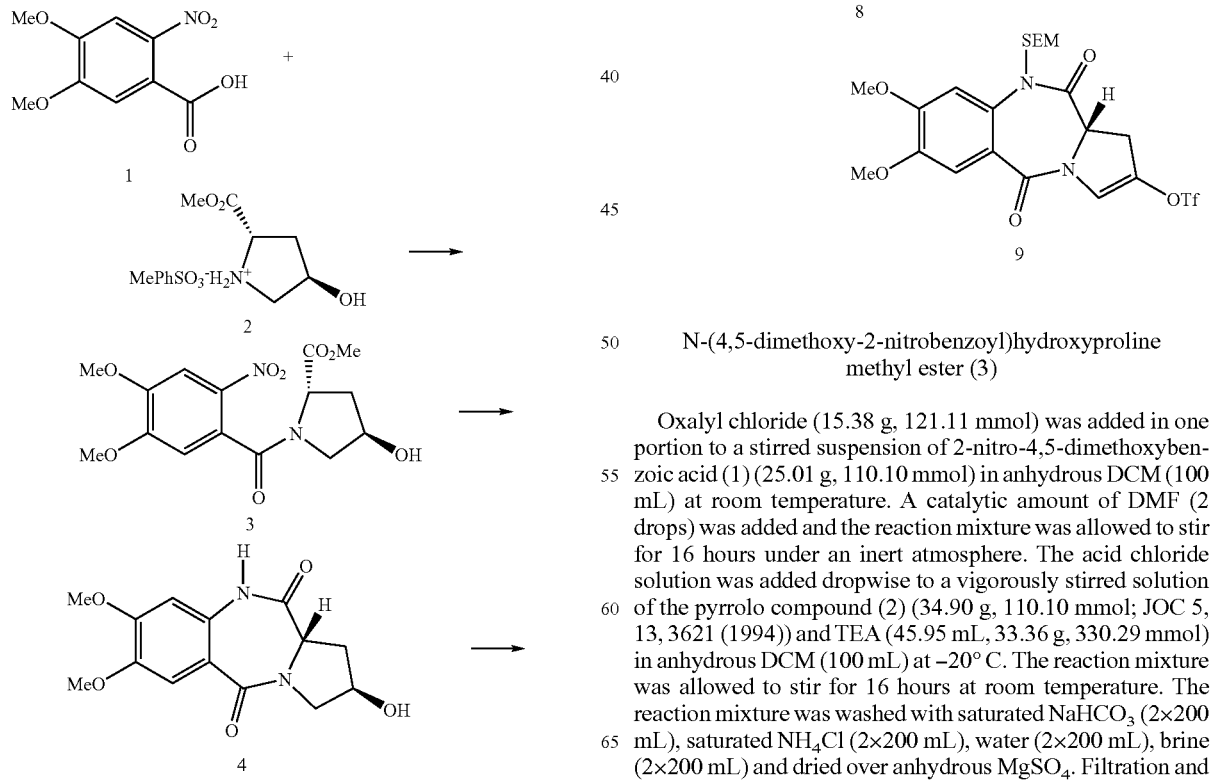

N-(4,5-dimethoxy-2-nitrobenzoyl)hydroxyproline methyl ester (3)

Oxalyl chloride (15.38 g, 121.11 mmol) was added in one portion to a stirred suspension of 2-nitro-4,5-dimethoxybenzoic acid (1) (25.01 g, 110.10 mmol) in anhydrous DCM (100 mL) at room temperature. A catalytic amount of DMF (2 drops) was added and the reaction mixture was allowed to stir for 16 hours under an inert atmosphere. The acid chloride solution was added dropwise to a vigorously stirred solution of the pyrrolo compound (2) (34.90 g, 110.10 mmol; JOC 5, 13, 3621 (1994)) and TEA (45.95 mL, 33.36 g, 330.29 mmol) in anhydrous DCM (100 mL) at −20° C. The reaction mixture was allowed to stir for 16 hours at room temperature. The reaction mixture was washed with saturated NaHCO$_3$ (2×200 mL), saturated NH$_4$Cl (2×200 mL), water (2×200 mL), brine (2×200 mL) and dried over anhydrous MgSO$_4$. Filtration and evaporation of the solvent in vacuo afforded the crude product (3), which was purified by flash column chromatography using EtOAc as eluent. Pure fractions were combined and evaporation of excess eluent in vacuo afforded the product as a foam (33.26 g, 93.9 mmol, 85%). $^1$H NMR (270 MHz, CDCl$_3$) δ 7.69 (s, 1H), 6.87 (s, 1H), 5.31 (s, 2H), 4.97-4.82 (m, 1H), 4.44 (br s, 1H), 3.99 (s, 3H), 3.98 (s, 3H), 3.81 (s, 3H), 3.54-3.48 (m, 1H), 3.18 (d, 1H, J=2.02 Hz), 2.87 (br s, 1H), 2.45-2.16 (m, 2H); $^{13}$C NMR (67.8 MHz, CDCl$_3$) δ 172.6, 172.5, 167.5, 166.8, 154.4, 154.0, 149.3, 137.5, 137.4, 127.0, 126.2, 109.5, 107.2, 107.1, 69.9, 69.1, 59.2, 57.4, 56.9, 56.8, 56.6, 56.4, 54.6, 53.5, 52.5, 52.4, 39.4, 38.0.

(11aS)-6,7-dimethoxy-2(R)-hydroxy-2,3,5,10,11, 11a-hexahydro-5,11-dioxo-1H-pyrrolo[2,1-c][1,4-]benzodiazepine (4)

10% Pd/C catalyst (3.3 g) was added to a solution of 3 (33.0 g, 93.1 mmol) in absolute EtOH (250 mL). The reaction mixture was hydrogenated under pressure using a Parr hydrogenator at 55 psi H$_2$ for 18 hours. The reaction mixture was filtered through celite, and the celite washed with hot MeOH, taking care not to allow the filter cake to dry out. Removal of excess solvent afforded the crude product (20.14 g). The crude product was allowed to stir in 1 N HCl (200 mL) and CHCl$_3$ (200 mL) for 30 minutes. The organic layer was washed with 1 N HCl (100 mL) and the aqueous layers were combined and neutralised with saturated aqueous NaHCO$_3$. On leaving the aqueous extract overnight, a fine white precipitate formed (4) which was collected by filtration and dried (7.81 g, 26.72 mmol, 29%). $^1$H NMR (270 MHz, CDCl$_3$) δ 10.06 (s, 1H, NH), 7.61 (s, 1H, ArH), 7.36 (s, 1H, ArH), 4.49-4.41 (m, 1H, 2), 4.22-4.17 (m, 1H, 11a), 3.88 (s, 6H), 3.82-3.55 (m, 2H, 3), 3.20 (br s, 1H, OH), 2.87-2.77 (m, 1H, 1), 2.10-2.05 (m, 1H, 1); $^{13}$C NMR (CDCl$_3$) δ 170.2, 165.9, 152.0, 145.7, 130.7, 118.2, 111.9, 104.2, 68.1, 56.0, 55.6, 54.2, 34.6, 18.8.

(11aS)-6,7-dimethoxy-2(R)-[(tert-butyldimethylsilyl)oxy]-2,3,5,10,11,11a-hexahydro-5,11-dioxo-1H-pyrrolo[2,1-c][1,4-]benzodiazepine (5)

Solid TBDMS Chloride (8.22 g, 54.44 mmol) was added in one portion to a solution of 4 (7.23 g, 24.74 mmol) and imidazole (8.42 g, 123.72 mmol) in anhydrous DMF (75 mL) and allowed to stir at room temperature for 16 hours. The reaction mixture was poured into water (500 mL) and filtered to afford the crude product (5), which was purified by recrystallisation from EtOH (800 mL) as fine white needles (6.995 g, 17.21 mmol, 70%). $^1$H NMR (270 MHz, CDCl$_3$) δ 10.06 (s, 1H, NH), 7.37 (s, 1H, ArH), 6.68 (s, 1H, ArH), 4.19-4.14 (m, 1H, 2), 4.06-4.01 (m, 1H, 11a), 3.90 (s, 3H, OMe), 3.88 (s, 3H, OMe), 3.69-3.63 (m, 2H, 3), 2.85-2.80 (m, 1H, 1), 2.05-2.01 (m, 1H, 1); $^{13}$C NMR (67.8 MHz, CDCl$_3$) δ 170.4, 170.2, 165.9, 152.1, 145.8, 145.6, 131.1, 130.7, 118.1, 111.9, 104.3, 104.1, 69.2, 69.1, 56.0, 55.9, 55.7, 54.3, 54.0, 35.0, 25.8, 25.7, 25.6, 17.9, −3.0, −3.5, −4.9, −5.0.

(11aS)-6,7-dimethoxy-2(R)-[(tert-butyldimethylsilyl) oxy]-2,3,5,10,11,11a-hexahydro-10-[2-(trimethylsilyl)ethoxymethyl]-5,11-dioxo-1H-pyrrolo[2,1-c][1,4-]benezodiazepine (6)

A solution of 5 (6.50 g, 15.99 mmol) in anhydrous DMF (27.5 mL) was added dropwise to a stirred suspension of NaH (0.422 g, 0.704 g of a 60% dispersion in mineral oil, 18.34 mmol) at 0° C. and the reaction mixture was allowed to stir for 30 minutes. A solution of SEM chloride (3.11 mL, 2.93 g, 17.59 mmol) in anhydrous DMF (5 mL) was added dropwise to the stirred reaction mixture at 0° C. and allowed to stir at room temperature for 16 hours. The reaction mixture was poured into water (200 mL) to afford a white precipitate, which was extracted with diethyl ether (4×300 mL). The organic layer was washed with water (2×50 mL), brine (2×50 mL) and dried over anhydrous MgSO$_4$. Filtration and evaporation of the solvent in vacuo afforded the crude product, which was purified by flash column chromatography using an 80:20 mixture of petroleum ether:EtOAc as eluent. Pure fractions were combined and evaporated in vacuo to afford the product (6) as a yellow oil (7.01 g, 13.1 mmol, 82%). $^1$H NMR (270 MHz, CDCl$_3$) δ 7.35 (s, 1H, ArH), 7.24 (s, 1H, ArH), 5.52 (d, 2H, J=9.89 Hz, SEM amino acetal CH$_2$), 4.65 (d, 2H, J=9.90 Hz, SEM amino acetal CH$_2$), 4.61-4.56 (m, 1H, 2), 4.23 (dd, 1H, J=4.40 Hz, 8.24 Hz, 11a), 3.94 (s, 3H, OMe), 3.92 (s, 3H, OMe), 3.68 (m, 4H, SEM 1=CH$_2$+3), 2.86 (m, 1H, 1), 2.02 (m, 1H, 1), 0.98 (t, 2H, J=8.25 Hz, SEM 2=CH$_2$), 0.88 (s, 9H, TBDMS t-Bu CH$_3$), 0.10 (s, 6H, 2×TBDMS SiCH$_3$), 0.03 (s, 9H, 3×SEM SiCH$_3$); $^{13}$C NMR (67.8 MHz, CDCl$_3$) δ 170.0, 165.6, 151.8, 147.1, 133.9, 121.5, 111.2, 105.5, 78.1, 69.6, 67.0, 56.5, 56.2, 56.1, 53.6, 35.5, 25.7, 18.4, −1.3, −4.8.

(11aS)-6,7-dimethoxy-2(R)-hydroxy-2,3,5,10,11, 11a-hexahydro-10-[2-(trimethylsilyl)ethoxymethyl]-5,11-dioxo-1H-pyrrolo[2,1-c][1,4-]benzodiazepine (7)

A solution of 1 N TBAF in THF (19.58 mL, 19.58 mmol) was added to a stirred solution of 6 (7.0 g, 13.05 mmol) in THF (50 mL). The reaction mixture was allowed to stir at room temperature for 2 hours and diluted with DCM (200 mL), washed with water (2×200 mL), brine (2×200 mL) and dried over anhydrous MgSO$_4$. Filtration and removal of excess solvent afforded the crude product, which was purified by flash column chromatography using 50:50 petroleum ether:EtOAc as eluent. Evaporation in vacuo of the pure fractions afforded the product (7) (5.9 g). $^1$H NMR (270 MHz, CDCl$_3$) δ 7.30 (s, 1H, ArH), 7.24 (s, 1H, ArH), 5.52 (d, 1H, J=9.9 Hz, SEM amino acetal CH$_2$), 4.68-4.64 (m, 2H, SEM amino acetal CH$_2$+2), 4.30 (dd, 1H, J=5.86, 8.24 Hz), 3.91 (s, 3H, OMe), 3.90 (s, 3H, OMe), 3.87-3.51 (m, 4H, SEM 1=CH$_2$+3), 2.95 (dt, 1H, J=5.31, 13.56 Hz, 1), 2.17-2.08 (m, 1H, 1), 1.02-0.93 (m, 2H, SEM 2=CH$_2$), 0.03 (s, 9H, 3×SiCH$_3$); $^{13}$C NMR (67.8 MHz, CDCl$_3$) δ 169.7, 165.9, 151.9, 147.1, 134.0, 121.1, 111.2, 105.5, 78.2, 69.1, 67.1, 56.5, 56.1, 53.9, 34.9, 18.4, −1.3.

(11aS)-6,7-dimethoxy-2,3,5,10,11,11a-hexahydro-10-[2-(trimethylsilyl) ethoxymethyl]-2,5,11-trioxo-1H-pyrrolo[2, 1-c][1,4-]benzodiazepine (8)

Anhydrous DMSO (3.28 g, 41.94 mmol) in dry DCM (20 mL) was added dropwise over 5 minutes to a stirred solution of oxalyl chloride (10.48 mL of a 2 N solution in DCM, 20.97 mmol) under a nitrogen atmosphere at −50° C. After stirring for 5 minutess, a solution 7 (5.90 g, 13.98 mmol), in dry DCM (45 mL) was added dropwise over 45 minutes to the reaction mixture, which was then stirred for a further 45 minutes at −50° C. TEA (9.89 g; 97.87 mmol) was added dropwise to the mixture over 15 minutes followed by stirring for a further 15 minutes. The reaction mixture was left to warm to room temperature, diluted with H$_2$O (150 mL) and DCM (100 mL). The organic phase was washed with 1 N HCl (2×100 mL), water (2×100 mL), brine (2×100 mL) and dried over MgS evaporation afforded the crude product (8), which was purified by flash column chromatography using 50:50 petroleum ether (40-60°):EtOAc as eluent. Evaporation of the pure fractions in vacuo afforded the product (4.33 g, 10.3 mmol, 74%). $^1$HNMR (270 MHz, CDCl$_3$) δ 7.30 (s, 1H, ArH), 7.24 (s, 1H, ArH), 5.60 (d, 1H, J=9.89 Hz, SEM amino acetal CH$_2$), 4.69 (d, 1H, J=9.89 Hz, SEM amino acetal CH$_2$), 4.62 (dd, 1H, J=9.89, 3.12 Hz, 11a), 4.26-4.19 (m, 1H, 3), 3.95 (s, 3HOHe), 3.94 (s, 3H, OMe), 3.81-3.49(m, 4H, SEM 1=CH$_2$+1+3), 2.82-2.71 (m, 1H, 1), 0.95 (t, 2H, J=2.01 Hz, SEM 2=CH$_2$), −0.04 (s, 9H, SEM CH$_3$); $^{13}$C NMR (67.8 MHz, CDCl$_3$) δ206.8, 168.8, 165.9, 152.4, 147.5, 134.0, 120.4, 111.1, 105.6, 78.2, 67.2, 56.2, 54.8, 52.3, 37.3, 18.3, −1.3.

(11aS)-5,10,11,11a-tetrahydro-7,8-dimethoxy-10-[2-(trimethylsilyl)ethoxymethyl]-2-[[(trifluoromethyl)sulphonyl]oxy]-5,11-dioxo-1H-pyrrolo[2, 1-c][1,4]benzodiazepine (9)

Anhydrous pyridine (0.46 mL, 0.452 g, 5.73 mmol) was added in one portion to a vigorously stirred solution of 8 (2.0 g, 4.77 mmol) in anhydrous DCM (100 mL) and the mixture left to stir for 10 minutes at room temperature. Anhydrous triflic anhydride (1.25 mL, 1.48 g, 5.25 mmol) was added quickly, in one portion, and the reaction mixture was allowed to stir at room temperature for 4.5 hours. The darkened, homogenous reaction mixture was poured into cold saturated NaHCO$_3$ (200 mL) and the mixture was extracted with DCM (3×50). The organic layers were combined, washed with water (2×200 mL), brine (2×200 mL) and dried over anhydrous MgSO$_4$. Filtration and evaporation afforded the crude product, which was purified by flash column chromatography using 80:20 petroleum ether:EtOAc as eluent. Evaporation of the pure fractions in vacuo afforded the product (9) as a yellow oil (1.79 g, 3.25 mmol, 68%). $^1$H NMR (270 MHz, CDCl$_3$) δ 7.29 (s, 1H, ArH), 7.23 (s, 1H, ArH), 7.15 (t, 1H, J=2.01 Hz, H3), 5.53 (d, 1H, J=10.07 Hz, SEM amino acetal CH$_2$), 4.68 (d, 1H, J=9.89 Hz, SEM amino acetal CH$_2$).

Example 1

Synthesis of (11aS)-1,11a-dihydro-7,8-dimethoxy-2-(2-napthyl)-5H-pyrrolo[2,1-c][1,4]benzodiazepin-5-one (11)

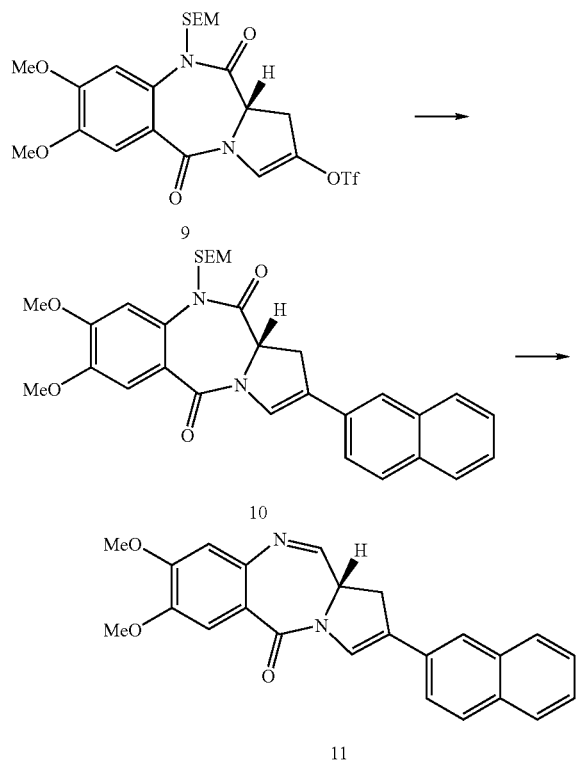

(a) 2-(2-napthyl)-7,8-dimethoxy-10-(2-trimethylsilanyl-ethoxymethyl)-1,11a-dihydro-5H-pyrrolo[2,1-c][1,4]benzodiazepine-5-one (10)

Sodium carbonate (300 mg, 2.83 mmol), 2-napthaleneboronic acid (171 mg, 0.99 mmol) and tetrakis(triphenylphosphine)palladium(0) (30 mg) were added to a solution of 9 (517 mg, 0.93 mmol) in ethanol/water/benzene (20/20/20 mL) and stirred at room temperature for 96 hours. The reaction mixture was diluted with ethyl acetate (220 mL) and washed with water (50 mL) and brine (50 mL) and dried over magnesium sulphate. The crude product was purified by flash column chromatography using 70% ethyl acetate in hexane as eluent to give the pure product 10 as a yellow oil.

$^1$H (250 MHz, CDCl$_3$) NMR: δ 7.85-7.71 (m, 4H, Ar—H×4), 7.67-7.54 (m, 2H, H-3, Ar—H×1), 7.52-7.39 (m, 3H, H-6, Ar—H×2), 7.33-7.27 (s, 1H, H-9), 5.58 (d, 1H, J=9.93 Hz, N—CH$_2$-OSEM×1), 4.79-4.66 (m, 2H, N—CH$_2$-OSEM×1, H-11a), 4.11 (d, 1H, J=16.28 Hz, H-1×1), 3.97 & 3.95 (2s, 6H, 7- & 8-MeO), 3.90-3.65 (m, 2H, O—CH$_2$-SEM), 3.28 (dd, 1H, J=10.92, 16.23 Hz, H-1×1), 1.00 (t, 2H, J=8.23 Hz, CH$_2$-SEM), 0.04 (s, 9H, SEM-Si(CH$_3$)$_3$)

(b) (11aS)-1,11a-dihydro-7,8-dimethoxy-2-(2-napthyl)-5H-pyrrolo[2,1-c][1,4]benzodiazepin-5-one (11)

Solid sodium tetraborohydride (654 mg, 17.2 mmol) was added in three portions at two hourly intervals to a stirred solution of 10 (971 mg, 1.8 mmol) in a mixture of anhydrous ethanol (19 mL) and anhydrous THF (37 mL) and left to stir at room temperature for 24 hours. The reaction mixture was diluted with water (50 mL) and extracted with ethyl acetate (3×50 mL). The organic layers were evaporated in vacuo. The crude product was treated with ethanol (50 mL), water (30 mL) and silica gel (18.3 g) and left to stir at room temperature for 24 hours. The reaction mixture was filtered and the product extracted with ethyl acetate (3×50). The organic layers were combined and washed with brine (20 mL) and dried over anhydrous magnesium sulphate. Filtration and evaporation in vacuo afforded the crude product, which was purified using flash column chromatography with a 70-50% hexane in ethyl acetate as eluent. Pure fractions were combined and evaporated in vacuo to afford the pure product 11 as a yellow powder (151 mg, 0.39 mmol, 22% yield).

$^1$H (250 MHZ, CDCL$_3$) NMR: δ 7.9 (d, 1H, J=4.0 Hz, H11), 7.86-7.40 (m, 8H, H3, H6, 6×Ar—H), 6.85 (s, 1H, H9), 4.48 (dt, 1H, J=4.9, 11.2 Hz, H11a), 3.98 & 3.95 (2s, 6H, 7- & 8-MeO), 3.80-3.46 (m, 2H, 2×H1).

Example 2

Synthesis of (11aS)-1,11a-dihydro-7,8-dimethoxy-2-(4-tert-butylbenzene)-5H-pyrrolo[2,1-c][1,4]benzodiazepin-5-one (13)

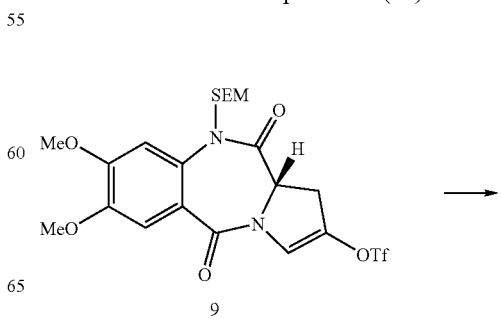

-continued

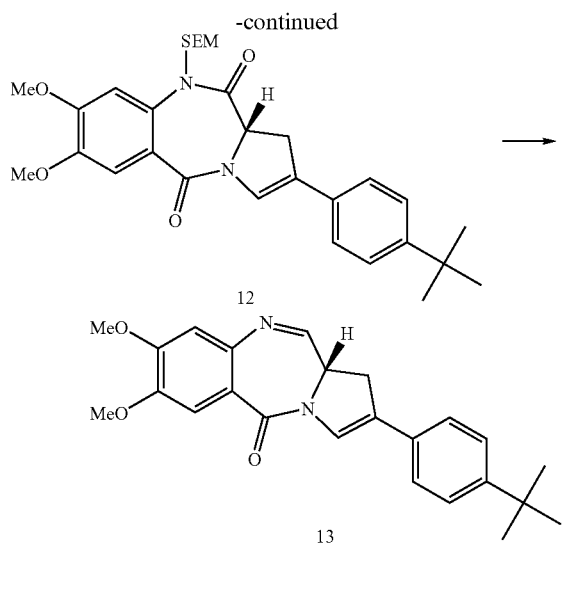

(a) 2-(4-tert-butylbenzene)-7,8-dimethoxy-10-(2-trimethylsilanyl-ethoxymethyl)-1,11a-dihydro-5H-pyrrolo[2,1-c][1,4]benzodiazepine-5-one (12)

Sodium carbonate (302 mg, 2.85 mmol), 4-tert-butylbenzeneboronic acid (177 mg, 0.99 mmol) and tetrakis(triphenylphosphine)palladium(0) (30 mg) were added to a solution of 9 (502 mg, 0.91 mmol) in ethanol/water/benzene (20/20/20 mL) and stirred at room temperature for 41 hours. The reaction mixture was diluted with ethyl acetate (220 mL) and washed with water (50 mL) and brine (50 mL) and dried over magnesium sulphate. The crude product was purified by automated flash column chromatography using a 100-50% hexane in ethyl acetate gradient system as eluent to give the pure product 12 (408 mg, 0.76 mmol, 84% yield).

$^1$H (250 MHz, CDCl$_3$) NMR: δ7.45-7.29 (m, 7H, H-6 & H-3 & H-9 & Ar—H×4), 5.56 (d, 1H, J=9.97 Hz, N—CH$_2$-OSEM×1), 4.78-4.55 (m, 2H, N—CH$_2$-OSEM×1, H-11a), 4.04-3.60 (m, 9H, 7- & 8-MeO and H-1×1 & O—CH$_2$-SEM), 3.16 (dd, 1H, J=10.35, 15.52 Hz, H-1×1), 1.38-1.21 (multiple singlets not all Me groups equivalent, 9H, tert-Bu (CH$_3$)$_3$), 1.04-0.80 (m, 2H, CH$_2$-SEM), 0.09-(-0.04) (multiple singlets not all Me groups equivalent, 9H, SEM-Si(CH$_3$)$_3$ (b) (11aS)-1,11a-dihydro-7,8-dimethoxy-2-(4-tert-butylbenzene)-5H-pyrrolo[2,1-c][1,4]benzodiazepin-5-one (13)

Sodium tetraborohydride (531 mg, 14.0 mmol) was added in three portions at 0, 5 and 30 hours to a stirred solution of 12 (398 mg, 0.74 mmol) in a mixture of anhydrous ethanol (7.5 mL) and anhydrous THF (15 mL). The reaction mixture was allowed to stir at room temperature for 44 hours. The reaction mixture was diluted with water (50 mL) and extracted with ethyl acetate (3×50 mL). The organic layers were evaporated in vacuo. The crude product was treated with ethanol (50 mL), water (25 mL) and silica gel (7.5 g) and left to stir at room temperature for 24 hours. The reaction mixture was filtered and the product extracted with ethyl acetate (3×50 ). The organic layers were combined and washed with brine (20 mL) and dried over anhydrous magnesium sulphate. Filtration and evaporation in vacuo afforded the crude product, which was purified using flash column chromatography with a 70%-50% hexane in ethyl acetate as eluent. Pure fractions were combined and evaporated in vacuo to afford the pure product 13 as yellow glassy solid (193 mg, 0.49 mmol, 67% yield).

$^1$H (250 MHZ, CDCL$_3$) NMR: δ 7.89 (d, 1H, J=3.94 Hz, H11), 7.58-7.17 (m, 6H, H3,H6, 4×Ar—H), 6.84 (s, 1H, H9), 4.49-4.35 (m, 1H, H11a), 4.05-3.51 (m, 7H, 7- & 8-MeO, H1), 3.49-3.33 (m, 1H, H1), 1.34 (s, 9H, Ar-tBu).

Example 3

Synthesis of (11aS)-1,11a-dihydro-7,8-dimethoxy-2-(4-chlorobenzene)-5H-pyrrolo[2,1-cl[]1,4]benzodiazepin-5-one (15)

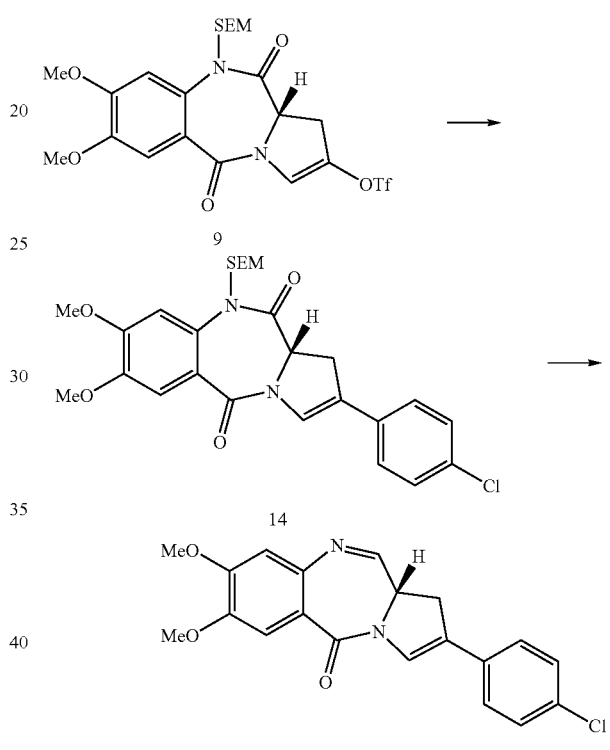

(a) 2-(4-chlorobenzene)-7,8-dimethoxy-10-(2-trimethylsilanyl-ethoxymethyl)-1,11a-dihydro-5H-pyrrolo[2,1-c][1,4]benzodiazepine-5-one (14)

Sodium carbonate (300 mg, 2.83 mmol), chlorobenzeneboronic acid (155.28 mg, 1.00 mmol) and tetrakis(triphenylphosphine)palladium(0)(30 mg) were added to a solution of 9 (500 mg, 0.90 mmol) in ethanol/water/benzene (20/20/20 mL) and stirred at room temperature for 46 hours at which point additional chlorobenzeneboronic acid (155 mg, 0.99 mmol) and tetrakis(triphenylphosphine)palladium(0) (30 mg) were added. The solution was stirred for a further 44 hours and then diluted with ethyl acetate (220 mL) and washed with water (50 mL) and brine (50 mL). The solution was dried over magnesium sulphate and purified by flash column chromatography using 70% ethyl acetate in hexane as eluent to give the pure product 14 as a brown oil (411 mg, 0.86 mmol, 95% yield).

$^1$H (250 MHz, CDCl$_3$) NMR : δ 7.46-7.22 (m, 7H, H-3 & H-6 & Ar—H×4 & H-9), 5.55 (d, 1H J=9.92 Hz, N—CH$_2$-

OSEM×1), 4.77-4.61 (m, 2H, N—CH$_2$-OSEM×1 & H-11a), 4.01-3.87 (m, 7H, H-1×1 and 7- & 8-MeO), 3.87-3.63 (m, 2H, O—CH$_2$-SEM), 3.13 (ddd, 1H, J=2.09, 10.56, 16.15 Hz, H-1×1), 0.98 (t, 2H, J=8.20 Hz, CH$_2$-SEM), 0.03 (s, 9H, SEM-Si(CH$_3$)$_3$).

(b) (11aS)-1,11a-dihydro-7,8-dimethoxy-2-(4-chlorobenzene)-5H-pyrrolo[2,1-c][1,4]benzodiazepin-5-one (15)

Sodium tetraborohydride (531mg, 14 mmol) was added in three portions at 0, 5 and 12 hours to a stirred solution of 14 (386 mg, 0.75 mmol) in a mixture of anhydrous ethanol (7.5 mL) and anhydrous TiHF (15 mL) and left to stir at room temperature for 24 hours. The reaction mixture was diluted with water (50 mL) and extracted with ethyl acetate (3×50 mL). The organic layers were evaporated in vacuo. The crude product was treated with ethanol (50 mL), water (25 mL) and silica gel (7.5 g) and left to stir at room temperature for 24 hours. The reaction mixture was filtered and the product extracted with ethyl acetate (3×50 ). The organic layers were combined and washed with brine (20 mL) and dried over anhydrous magnesium sulphate. Filtration and evaporation in vacuo afforded the crude product, which was purified using flash column chromatography with a 70%-50% hexane in ethyl acetate as eluent. Pure fractions were combined and evaporated in vacuo to afford the pure product 15 as a yellow solid (97.5 mg, 0.26 mmol, 35% yield).

$^1$H (250 MHZ, CDCL$_3$) NMR: δ 7.90 (d, 1H, J=3.9 Hz, H11), 7.53 (s, 1H, H6), 7.50 (broad s, 1H, H3), 7.32 (s, 4H, 4×Ar—H), 6.84 (s, 1H H9), 4.44 (ddd, 1H, J=4.1, 5.3, 11.4 Hz, H11a), 3.97 & 3.95 (2s, 6H, 7- & 8-MeO), 3.58 (ddd, 1H, J=1.98, 11.6, 16.3 Hz, H1), 3.4 (ddd, 1H, J=1.7, 5.4, 16.3 Hz, H1).

Example 4

Synthesis of (11aS)-1,11a-dihydro-7,8-dimethoxy-2-(4-fluorobenzene)-5H-pyrrolo[2,1-c][1,4]benzodiazepin-5-one (17)

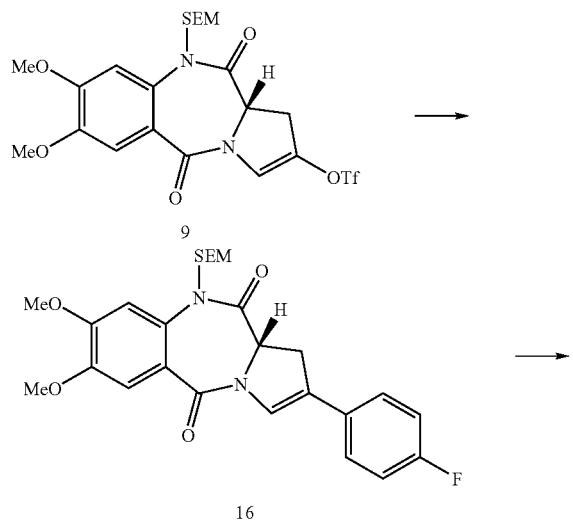

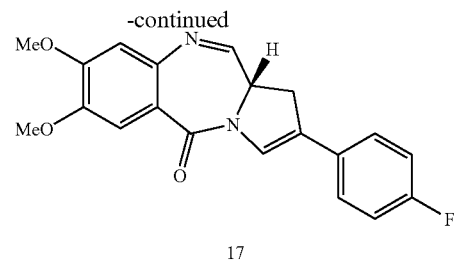

(a) 2-(4-fluorobenzene)-7,8-dimethoxy-10-(2-trimethylsilanyl-ethoxymethyl)-1,11a-dihydro-5H-pyrrolo[2,1-c][1,4]benzodiazepine-5-one (16)

Sodium carbonate (308 mg, 2.91 mmol), 4-fluorobenzeneboronic acid (139 mg, 0.99 mmol) and tetrakis(triphenylphosphine) palladium(0) (30 mg) were added to a solution of 9 (500 mg, 0.90 mmol) in ethanol/water/benzene (20/20/20 mL) and stirred at room temperature for 93 hours. The reaction mixture was diluted with ethyl acetate (220 mL) and washed with water (50 mL) and brine (50 mL) and dried over magnesium sulphate. The crude product was purified by automated flash column chromatography using a 100 -50% hexane in ethyl acetate gradient system as eluent to give the pure product 16 as a yellow oil (441 mg, 0.88 mmol, 99% yield).

$^1$H (250 MHz, CDCl$_3$) NMR: δ 7.45-7.32 (m, 5H, H-6 & H-3 & Ar—H×2), 7.27 (s, 1H, H-9), 7.04 (t, 2H, Ar—H×2), 5.56 (d, 1H, J=9.80 Hz, N—CH$_2$-OSEM×1), 4.72 (d, 1H, J=9.49 Hz, N—CH$_2$-OSEM×1), 4.65 (dd, 1H, J=3.28, 10.17 Hz, H-11a), 4.04-3.88(m, 7H, 7- & 8-MeO and H-1×1), 3.88-3.64 (m, 2H, O—CH$_2$-SEM), 3.14 (ddd, 1H, J=2.26, 10.57, 16.25 Hz, H-1×1), 0.99 (t, 2H, J=8.33 Hz, CH$_2$-SEM), 0.03 (s, 9H, SEM-Si(CH$_3$)$_3$).

(b) (11aS) -1,11a-dihydro-7,8-dimethoxy-2-(4-fluorobenzene) -5H-pyrrolo[2,1-c][1,4]benzodiazepin-5-one (17)

Sodium tetraborohydride (201mg, 5.3 mmol) was added in two portions at 0 and 5 hours to a stirred solution of 16 (429 mg, 0.861 mmol) in a mixture of anhydrous ethanol (8.6 mL) and anhydrous THF (17.2 mL). The reaction mixture was allowed to stir at room temperature for 24 hours. The reaction mixture was diluted with water (50 mL) and extracted with ethyl acetate (3×50 mL). The organic layers were evaporated in vacuo. The crude product was treated with ethanol (50 mL), water (25 mL) and silica gel (8.6 g) and left to stir at room temperature for 24 hours. The reaction mixture was filtered and the product extracted with ethyl acetate (3×50 ). The organic layers were combined and washed with brine (20 mL) and dried over magnesium sulphate. Filtration and evaporation in vacuo afforded the crude product, which was purified using flash column chromatography with a 70%-50% hexane in ethyl acetate as eluent. Pure fractions were combined and evaporated in vacuo to afford the pure product 17 as a yellow glassy solid (139 mg, 0.39 mmol, 46% yield).

$^1$H (250 MHZ, CDCL$_3$) NMR: δ 7.90 (d, 1H, J=3.9 Hz, H11), 7.53 (s, 1H, H6), 7.45 (s, 1H, H3), 7.40-7.20 (m, 1H, 1 ×Ar—H), 7.10-6.90 (m, 3H, 3 ×Ar—H), 6.84 (s, 1H, H9), 4.43 (ddd, 1H, J=4.1, 5.4, 11.4 Hz, H11a), 3.97 & 3.95 (2s, 6H, 7- & 8-MeO), 3.69-3.50 (m, 1H, H1), 3.39 (ddd, 1H, J=1.5, 5.3, 16.3 Hz, H1).

Example 5

Synthesis of (11aS)-1,11a-dihydro-7,8-dimethoxy-2-(2-methylbenzene)-5H-pyrrolo[2,1-c][1,4]benzodiazepin-5-one (19)

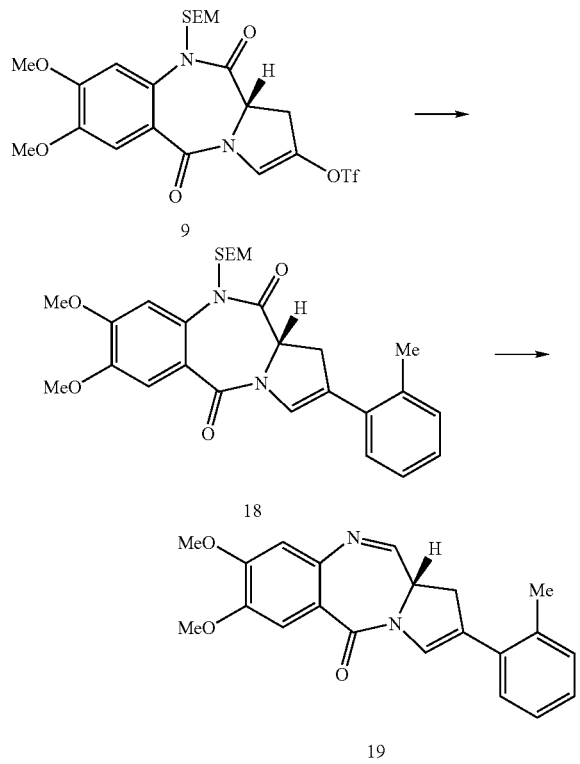

(a) 2-(2-methylbenzene)J-7,8-dimethoxy-10-(2-trimethylsilanyl-ethoxymethyl)-1,11a-dihydro-5H-pyrrolo[2,1-c][1,4]benzodiazepine-5-one (18)

Sodium carbonate (300 mg, 2.83 mmol), 2-methylbenzeneboronic acid (135 mg, 0.99 mmol) and tetrakis(triphenylphosphine)palladium(0) (30 mg) were added to a solution of 9 (500 mg, 0.90 mmol) in ethanol/water/benzene (20/20/20 mL) and stirred at room temperature for 20 hours. The reaction mixture was diluted with ethyl acetate (200 mL) and washed with water (50 mL) and brine (50 mL) and dried over magnesium sulphate. The crude product was purified by automated flash column chromatography using a 100-50% hexane in ethyl acetate gradient system as eluent to give the pure product 18 as a yellow oil (439 mg, 0.89 mmol, 98% yield).

$^1$H (250 MHz, CDCl$_3$) NMR: δ 7.44-7.09 (m, 7H, H-6 & H-3 & H-9 & Ar—H×4), 5.59 (d, 1H, J=9.97 Hz, N—CH$_2$-OSEM ×1), 4.78-4.50 (m, 2H, N—CH$_2$-OSEM×1, H-11a), 4.06-3.60 (m, 9H, 7- & 8-MeO, O—CH$_2$-SEM, H-1×1), 3.22 (dd, 1H, J=10.23, 16.31 Hz, H-1×1), 2.48 (Broad s, 3H, Ar-2-Me), 1.06-0.79 (m, 2H, CH$_2$-SEM), 0.03 (broad s, 9H, SEM-Si(CH$_3$)$_3$).

(b) (11aS)-1,11a-dihydro-7,8-dimethoxy-2-(2-methylbenzene)-5H-pyrrolo[2,1-c][1,4]benzodiazepin-5-one (19)

Sodium tetraborohydride (500 mg, 13.2 mmol) was added in three portions at 0, 5 and 12 hours to a stirred solution of 18 (429 mg, 0.87 mmol) in a mixture of anhydrous ethanol (8.5 mL) and anhydrous THF (17.5 mL). The reaction mixture was allowed to stir at room temperature for 24 hours. The reaction mixture was diluted with water (50 mL) and extracted with ethyl acetate (3×50 mL). The organic layers were evaporated in vacuo. The crude product was treated with ethanol (50 mL), ice water (25 mL) and silica gel (8.5 g) and left to stir at room temperature for 24 hours. The reaction mixture was filtered and the product extracted with ethyl acetate (3×50 mL). The organic layers were combined and washed with brine (20 mL) and dried over anhydrous magnesium sulphate. Filtration and evaporation in vacuo afforded the crude product, which was purified using flash column chromatography with a 70%-50% hexane in ethyl acetate as eluent. Pure fractions were combined and evaporated in vacuo to afford the pure product 19 as a yellow solid (74 mg, 0.21 mmol, 25% yield).

$^1$H (250 MHZ, CDCL$_3$) NMR: δ7.92 (d, 1H, J=3.9 Hz, H11), 7.55 (s, 1H, H6), 7.34-7.14 (m, 5H, H3, 4 ×Ar—H), 6.85 (s, 1H, H9), 4.39 (dt, 1H, J=4.7, 11.4 Hz, H11a), 3.97 & 3.95 (2s, 6H, 7- & 8-MeO), 3.78-3.59 (m, 1H, H1), 3.47 (dd, 1H J=5.2, 16.2 Hz, H1), 2.49 (s, 3H, Ar—CH$_3$).

Example 6

Synthesis of (11aS)-1,11a-dihydro-7,8-dimethoxy-2-(2-methylbenzene)-5H-pyrrolo[2,1-c][1,4]benzodiazepine-5-one (21)

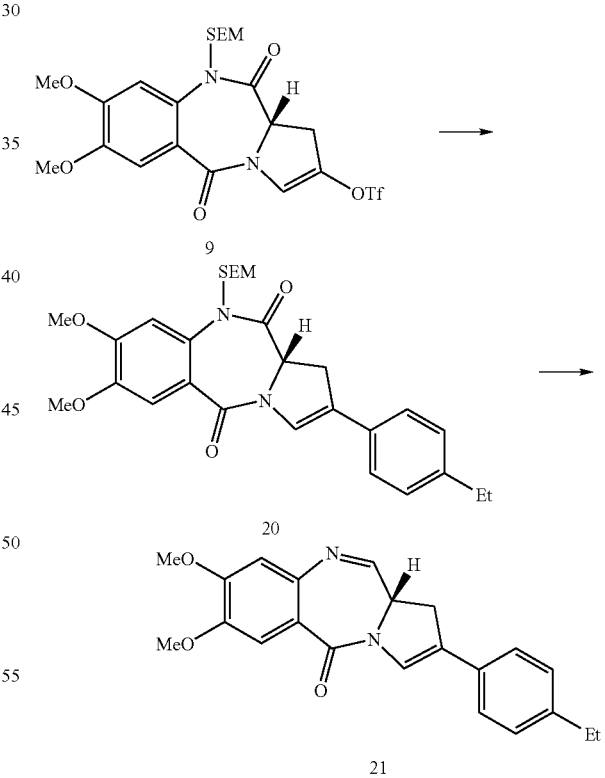

(a) 2-(4-ethylbenzene)-7,8-dimethoxy-10-(2-trimethylsilanyl-ethoxymethyl)-1,11a-dihydro-5H-pyrrolo[2,1][1,4]benzodiazepine-5-one (20)

Sodium carbonate (302 mg, 2.85 mmol), 4-ethylbenzeneboronic acid (149 mg, 0.993 mmol) and tetrakis(triphenylphosphine) palladium(0) (30 mg) were added to a solution of 9 (501 mg, 0.91 mmol) in ethanol/water/benzene (20/20/20 mL) and stirred at room temperature for 41 hours. The reaction mixture was diluted with ethyl acetate (220 mL) and washed with water (50 mL) and brine (50 mL) and dried over magnesium sulphate. The crude product was purified by automated flash column chromatography using a 100 -50% hexane in ethyl acetate gradient system as eluent to give the pure product 20 as a yellow solid (342 mg, 0.67 mmol, 74% yield).

$^1$H (250 MHz, CDCl$_3$) NMR: δ 7.46-7.15 (m, 7H, H-6 & H-3 & H-9 & Ar—H×4), 5.57 (d, 1H, J=9.88 Hz, N—CH$_2$-OSEM×1), 4.72 (d, 1H, J=9.95 Hz, N—CH$_2$-OSEM×1), 4.65 (dd, 1H, J=3.52, 10.85 Hz, H-11a), 4.03-3.88 (m, 7H, 7- & 8-Meo and H-1×1), 3.88-3.64 (m, 2H, O—CH$_2$-SEM), 3.16 (dd, 1H, J=10.84, 16.51 Hz, H-1×1), 2.66 (q, 2H, J=7.68 Hz, Ar—CH$_2$-Me×2), 1.24 (t, 3H, J=7.57 Hz, ArCH$_2$—CH$_3$), 0.99 (t, 2H, J=8.29 Hz, CH$_2$-SEM), 0.04 (s, 9H, SEM—Si(CH$_3$)$_3$).

(b) (11aS)-1,11a-dihydro-7,8-dimethoxy-2-(2-methylbenzene)-5H-pyrrolo[2,1-c][1,4]benzodiazepin-5-one (21)

Sodium tetraborohydride (500 mg, 13.2 mmol) was added in three portions at 0, 5 and 12 hours to a stirred solution of 20 (429 mg, 0.87 mmol) in a mixture of anhydrous ethanol (8.5 mL) and anhydrous THF (17.5 mL). The reaction mixture was allowed to stir at room temperature for 24 hours. The reaction mixture was diluted with water (50 mL) and extracted with ethyl acetate (3×50 mL). The organic layers were evaporated in vacuo. The crude product was treated with ethanol (50 mL), ice water (25 mL) and silica gel (8.5 g) and left to stir at room temperature for 24 hours. The reaction mixture was filtered and the product extracted with ethyl acetate (3×50 ). The organic layers were combined and washed with brine (20 mL) and dried over anhydrous magnesium sulphate. Filtration and evaporation in vacuo afforded the crude product, which was purified using flash column chromatography with a 70%-50% hexane in ethyl acetate as eluent. Pure fractions were combined and evaporated in vacuo to afford the pure product 21 as a yellow solid (74 mg, 0.21 mmol, 25% yield).

$^1$H (250 MHZ, CDCL$_3$) NMR: δ 7.92 (d, 1H, J=3.9 Hz, H11), 7.55 (s, 1H, H6), 7.34-7.14 (m, 5H, H3, 4 ×Ar—H), 6.85 (s, 1H, H9), 4.39 (dt, 1H, J=4.7, 11.4 Hz, H11a), 3.97 & 3.95 (2s, 6H, 7- & 8-MeO), 3.78-3.59 2.49 (s, 3H, Ar—CH$_3$).

Example 7

Synthesis of (11aS)-1,11a-dihydro-7,8-dimethoxy-2-(2-thiophene)-5H-pyrrolo[2,1-c][1,4]benzodiazepin-5-one (23)

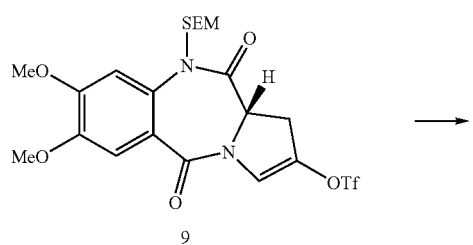

9

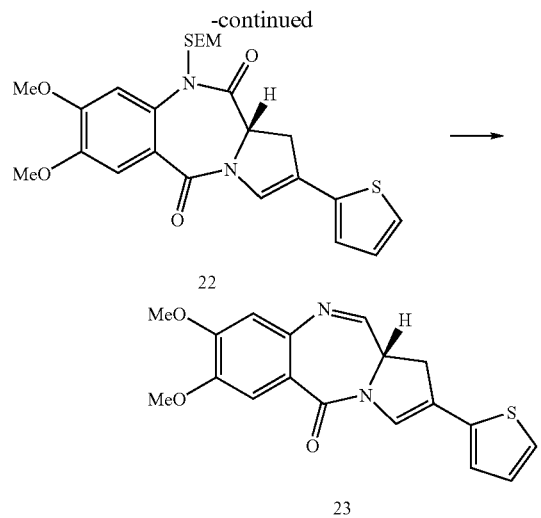

22

23

(a) 2-(2-thiophene)-7,8-dimethoxy-10-(2-trimethylsilanyl-ethoxymethyl)-1,11a-dihydro-5H-pyrrolo[2,1-c][1,4]benzodiazepine-5-one (22)

Sodium carbonate (305 mg, 2.88 mmol), 2-thiopheneboronic acid (127 mg, 0.99 mmol) and tetrakis(triphenylphosphine) palladium(0) (30 mg) were added to a solution of 9 (500 mg, 0.90 mmol) in ethanol/water/benzene (20/20/20 mL) and stirred at room temperature for 164.5 hours and refluxed at 80° C. for a further 4 hours. The reaction mixture was diluted with ethyl acetate (200 mL) and washed with water (50 mL) and brine (50 mL) and dried over magnesium sulphate. The crude product was purified by automated flash column chromatography using a 100-50% hexane in ethyl acetate gradient system as eluent to give the pure product 22 as a yellow oil (353 mg, 0.73 mmol, 80% yield).

$^1$H (250 MHz, CDCl$_3$) NMR : δ 7.39 (s, 1H, H-6), 7.32-7.17 (m, 3H, H-3, H-9, Ar—H×1), 7.06-6.94 (m, 2H, Ar—H×2), 5.56 (d, 1H, J=9.97 Hz, N—CH$_2$-OSEM×1), 4.71 (d, 1H, J=9.91 Hz, N—CH$_2$-OSEM×1), 4.64 (dd, 1H, J=3.51, 10.56 Hz, H-11a), 4.02-3.88 (m, 7H, 7- & 8-MeO, H-1×1), 3.88-3.63 (m, 2H, O—CH$_2$-SEM), 3.18 (ddd, 1H, J=2.38, 10.76, 16.11 Hz, H-1×1), 0.99 (t, 2H, J=8.24 Hz, CH$_2$-SEM), 0.04 (s, 9H, SEM-Si(CH$_3$)$_3$).

(b) (11aS)-1,11a-dihydro-7,8-dimethoxy-2-(2-thiophene)-5H-pyrrolo [2,1-c][1,4]benzodiazepin-5-one (23)

Sodium tetraborohydride (520 mg, 13.7 mmol) was added in three portions at 0, 7 and 14 hours to a stirred solution of 22 (333 mg, 0.69 mmol) in a mixture of anhydrous ethanol (6.9 mL) and anhydrous THF (13.8 mL) and left to stir at room temperature for 30 hours. The reaction mixture was diluted with water (50 mL) and extracted with ethyl acetate (3×50 mL). The organic layers were evaporated in vacuo and the crude product was treated with ethanol (50 mL), water (25 mL) and silica gel (6.9 g) and left to stir at room temperature for 24 hours. The reaction mixture was filtered and the product extracted with ethyl acetate (3×50 mL). The organic layers were combined and washed with brine (20 mL) and dried over anhydrous magnesium sulphate. Filtration and evaporation in vacuo afforded the crude product, which was purified using flash column chromatography with a 70%-50% hexane in ethyl acetate as eluent. Pure fractions were combined and evaporated in vacuo to afford the pure product 23 as a yellow solid (49.6 mg, 0.15 mmol, 21% yield).

MS (ES) m/z(relative intensity): 389.2 (22), 373.2 (14), 341 (8), 194.3 (100).

Example 8

Synthesis of (11aS)-1,11a-dihydro-7,8-dimethoxy-2-(2-furan)-5H-pyrrolo[2,1-c][1,4]benzodiazepin-5-one (25)

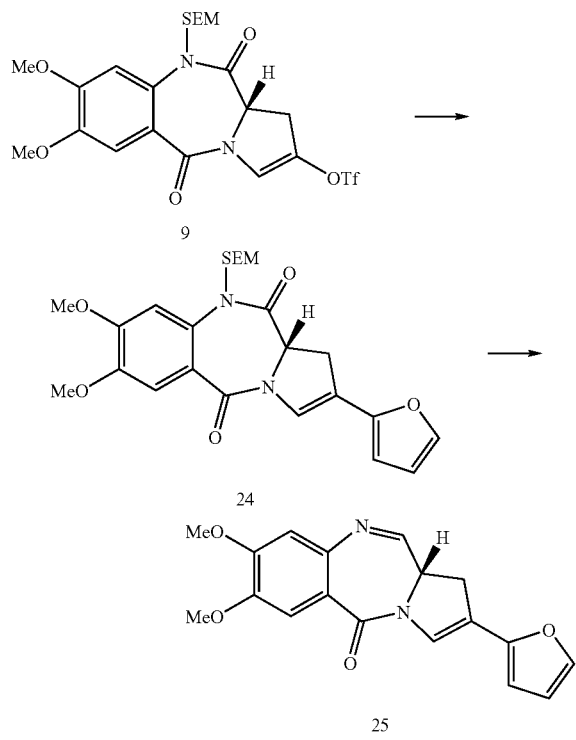

(a) 2-(2-furan)-7,8-dimethoxy-10-(2-trimethylsilanyl-ethoxymethyl)-1,11a-dihydro-5H-pyrrolo[2,1-c][1,4]benzodiazepine-5-one (24)

A catalytic amount of tetrakis triphenylphosphine palladium [0] (5 mol %, 73 mg, 0.063 mmol) was added to a stirred mixture of 9(700 mg, 1.27 mmol), LiCl (161 mg, 3.8 mmol), and 2-(tributylstannyl)furan (0.526 mL, 615 mg, 1.65 mmol) in anhydrous THF (20 mL) and heated at reflux for 2 ½ hours. The cooled reaction mixture was diluted with DCM (100 mL) and the mixture washed with 10% aqueous ammonium hydroxide (100 mL). The organic layer was washed with water (100 mL), brine (100 mL), and dried over anhydrous $MgSO_4$. Filtration and evaporation of the solvent in vacuo afforded the crude product, which was further purified by flash chromatography using a 75:25 mixture of hexane:EtOAc as eluent. Pure fractions were combined and evaporation of the solvent in vacuo afforded the product 24 (484 mg, 1.03 mmol, 81%).

$^1$H NMR (CDCl$_3$) δ 7.35 (s, 2H), 7.27 (s, 1H),7.23 (d, J$_1$=1.5 Hz, 1H), 6.37 (dd,J$_1$=1.7 Hz, J$_2$=3.2 Hz, 1H), 6.26 (d, J$_1$=3.2 Hz), 5.52 (d, J=10 Hz, 1H, SEM), 4.67 (d, J=10 Hz, 1H, SEM), 4.58 (dd, J$_1$=3.3 Hz, J$_2$=10.6 Hz, 1H, H11a), 3.91 (s, 3H, OMe), 3.90 (s, 3H, OMe), 3.86-3.74 (m, 2H, 1SEM, 1H1), 3.69-3.63 (m, 1H, 1SEM), 3.05 (ddd, J$_1$=2.0 Hz, J$_2$=10.6 Hz, J$_3$=15.8 Hz, 1H1), 0.95 (m, 2H, SEM), 0 (s, 9H, SEM).

$^{13}$C NMR (CDCl$_3$) δ 169.5, 163, 153.4, 150.6, 148.7, 143.7, 135, 122.6, 122.4, 117.7, 112.7, 108.6, 107.2, 79.7, 68.51, 58.75, 57.5, 31.8, 19.7, 0

IR 2952, 1689, 1640, 1606, 1518, 1453, 1430, 1358, 1276, 1248, 1209, 1102, 1069, 1010, 858, 836, 787, 757.

MS ES$^+$471.2 (M+H, 100%), 353.1 (65%). [α]$_d$=+175°, c=20mg/10 mL, T=18.6° C., CHCl$_3$.

(b) (11aS)-1,11a-dihydro-7,8-dimethoxy-2-(2-furan)-5H-pyrrolo[2,1-c][1,4]benzodiazepin-5-one (25)

Solid sodium tetraborohydride (NaBH$_4$, 95 mg, 2.51 mmol) was added in one portion to a rapidly stirred solution of 24 (400 mg, 0.85 mmol) in a mixture of anhydrous EtOH (3 mL) and anhydrous THF (7 mL) at room temperature and allowed to stir for 4 hours. More sodium tetraborohydride (60 mg, 1.58 mmol) was added and the mixture left to stir at room temperature overnight. The reaction mixture was diluted with cold water (50 mL) and extracted with EtOAc (2×30 mL). The organic layers were washed with brine (30 mL) and dried over anhydrous MgSO$_4$. Filtration and evaporation of the solvent in vacuo afforded the crude product which was stirred overnight with silica gel (1 g) in EtOH (10 mL) and water (5 mL). The mixture was then filtered and excess EtOH was removed by rotary evaporation. The remaining mixture was extracted with EtOAc (2×20 mL). The organic layers were washed with brine (30 mL) and dried over anhydrous MgSO$_4$. Filtration and evaporation of the solvent in vacuo afforded the crude product which was purified by flash column chromatography eluting with a 60:40 mixture of hexane:EtOAc. Pure fractions were combined to afford 25 as a yellow solid (80 mg, 0.246 mmol, 29%).

$^1$H NMR (CDCl$_3$) δ 7.89 (d, J=4.0 Hz, 1H, H-11), 7.54 (s, 1H),7.42 (d, J=1.4 Hz, 1H), 7.38 (s, 1H), 6.84 (s, 1H) 6.44 (dd, J$_1$=1.7 Hz, J$_2$=3.2 Hz, 1H), 6.28 (d, J=3.2 Hz, 1H), 4.41 (m, 1H, H11a), 3.98 (s, 3H, MeO), 3.96 (s, 3H, MeO), 3.50(m, 1H1), 3.35 (ddd, J$_1$=1.6 Hz, J$_2$=5.2 Hz, J$_2$=16.2 Hz, 1H, 1H1).

$^{13}$C NMR (CDCl$_3$) δ 163.8, 162.8, 153.4, 150.7, 149.3, 143.9, 141.8, 124.3, 120.5, 115.8, 113.1, 112.9, 111.3, 108.2, 57.7, 57.6, 55.2, 36.

IR 3117, 2936, 1626, 1601, 1559, 1508, 1450, 1426, 1377, 1344, 1265, 1215, 1102, 1072, 1039, 1007, 956, 914, 882, 778, 730.

MS ES$^+$325.1 (M+H, 100%).

[α]$_d$=+457°, c=15 mg/10 mL, T=20° C. CHCl$_3$

Example 9

Synthesis of (11aS)-1,11a-dihydro-7,8-dimethoxy-2-(2,6-dimethylbenzene)-5H-pyrrolo[2,1-c][1,4]benzodiazepin-5-one (27)

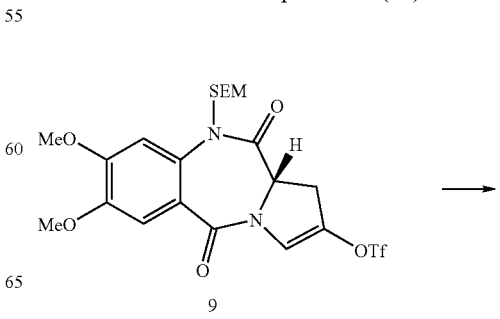

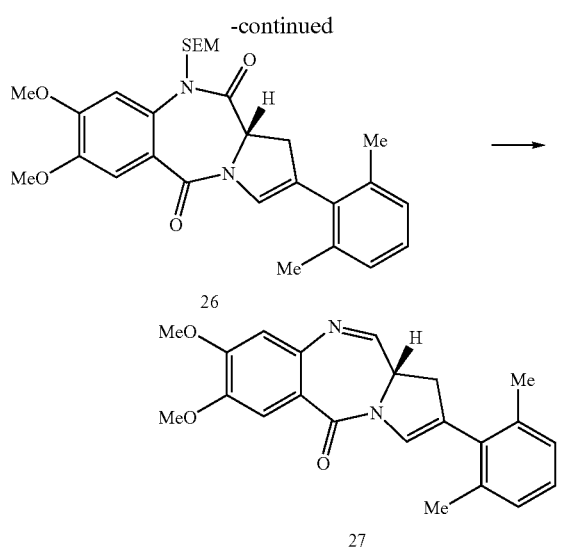

(a) 2-(2,6-dimethylbenzene)-7,8-dimethoxy-10-(2-trimethylsilanyl-ethoxymethyl)-1,11a-dihydro-5H-pyrrolo[2,1-c][1,4]benzodiazepine-5-one (26)

Sodium carbonate (300 mg, 2.85 mmol), 2,6-dimethylbenzeneboronic acid (149 mg, 0.99 mmol) and tetrakis(triphenylphosphine)palladium(0) (30 mg) were added to a solution of 9 (500 mg, 0.90 mmol) in ethanol/water/benzene (2/2/6 mL) and stirred at room temperature for 306.5 hours. The reaction mixture was diluted with ethyl acetate (50 mL) and washed with water (20 mL) and brine (20 mL) and dried over magnesium sulphate. The crude product was purified by automated flash column chromatography using a 100-50% hexane in ethyl acetate gradient system as eluent to give the pure product (218 mg, 0.43 mmol, 47% yield).

$^1$H (250 MHz, CDCl$_3$) NMR: δ 7.42 (s, 1H, H-6), 7.28 (s, 1H, H-9), 7.22-7.02 (m, 3H, Ar—H×3), 6.82 (broad s, 1H, H-3), 5.62 (d, 1H, J=9.85 Hz, N—CH$_2$-OSEM×1), 4.74 (d, 1H, J=9.72 Hz, N—CH$_2$-OSEM×1), 4.64 (dd, 1H, J=3.08, 10.51 Hz, H-11a), 3.96 & 3.94 (2s, 6H, 7- & 8-MeO), 3.89-3.64 (m, 3H, O—CH$_2$-SEM, H-1×1), 3.02 (ddd, 1H, J=2.39, 10.58, 16.89 Hz, H-1×1), 2.32 (s, 6H, Ar-2,6-diMe×6), 1.00 (t, 2H, J=8.27 Hz, CH$_2$-SEM), 0.03 (s, 9H, SEM-Si(CH$_3$)$_3$).

(b) (11aS)-1,11a-dihydro-7,8-dimethoxy-2-(2,4-dimethyl-benzene)-5H-pyrrolo[2,1-c][1,4]benzodiazepin-5-one (27)

Solid sodium tetraborohydride (276 mg, 7.3 mmol) was added in two portions at 0 and 24 hours to a stirred solution of 26 (208 mg, 0.41 mmol) in a mixture of anhydrous ethanol (4.1 mL) and anhydrous THF (8.2 mL). The reaction mixture was allowed to stir at room temperature for 47 hours. The reaction mixture was diluted with water (50 mL) and extracted with ethyl acetate (3×50 mL). The organic layers were evaporated in vacuo and the crude product was treated with ethanol (50 mL), ice water (25 mL) and silica gel (8.2 g) and left to stir at room temperature for 24 hours. The reaction mixture was filtered and the product extracted with ethyl acetate (3×50 mL). The organic layers were combined and washed with brine (20 mL) and dried over anhydrous magnesium sulphate. Filtration and evaporation in vacuo afforded the crude product, which was purified using flash column chromatography with a 70%-50% hexane in ethyl acetate as eluent. Pure fractions were combined and evaporated in vacuo to afford the pure product 27 as a yellow solid (43.3 mg, 0.12 mmol, 29% yield).

$^1$H (250 MHZ, CDCL$_3$) NMR: δ 7.92 (d, 1H, J=3.9 Hz, H11), 7.55 (s, 1H, H6), 7.34-7.14 (m, 5H, H3, 4×Ar—H), 6.85 (s, 1H, H9), 4.39 (dt, 1H, J=4.7, 11.4 Hz, H11a), 3.97 & 3.95 (2s, 6H, 7- & 8-MeO), 3.78-3.59 (m, 1H, H1), 3.47 (dd, 1H, J=5.2, 16.2 Hz, H1), 2.49 (s, 6H, Ar—CH$_3$).

Biological Assays

In Vitro-Clonogenic Cell Lines

In order to determine the activity of the compounds synthesised, solid human tumour xenografts growing subcutaneously in serial passages in thymus aplastic nude mice (Naval Medical Research Institute, USA nu/nu strain) were removed under sterile condition, mechanically disaggregated and subsequently incubated with an enzyme cocktail consisting of collagenase (41 U/ml, Sigma), DNAse I (125 U/ml, Roche), hyaluronidase (1000 U/ml, Sigma) and dispase II (1.0 U/ml) in RPMI 1640-Medium (Life Technologies) at 37° C. for 30 minutes. Cells were passed through sieves of 200 μm and 50 μm mesh size and washed twice with sterile PBS-buffer. The percentage of viable cells was determined in a Neubauer-hemocytometer using trypan blue exclusion. The cells generated were as follows:

Breast MACL MCF7
Renal 9442
Lung 629L
Melanoma MEXF 462NL

The clonogenic assay was performed in a 24-well format according to a modified two-layer agar assay introduced by Hamburger, A. W. and Salmon, S. E., *Science,* 197, 461-643 (1977). The bottom layer consisted of 0.2 ml/well of Iscove's Modified Dulbecco's Medium (supplemented with 20% fetal calf serum and 1% gentamicin) and 0.75% agar. 4×10$^4$ to 8×10$^4$ cells were added to 0.2 ml of the same culture medium supplemented with 0.4% agar and plated in 24-multiwell dishes onto the bottom layer. The test compounds were applied by continuous exposure (drug overlay) in 0.2 ml culture medium. Each dish included six control wells containing the vehicle and drug treated groups in triplicate at 6 concentrations. Cultures were incubated at 37° C. and 7.5% CO2 in a humidified atmosphere for 8-20 days and monitored closely for colony growth using an inverted microscope. Within this period, in vitro tumour growth led to the formation of colonies with a diameter of >50 μm. At the time of maximum colony formation, counts were performed with an automatic image analysis system (OMNICOM FAS IV, Biosys GmbH). 24 hours prior to evaluation, vital colnies were stained with a sterile aqueous solution of 2-(4-iodophenyl)-3-(4-nitrophenyl)-5-phenyltetrazolium chloride (1 mg/ml, 100 μl/well).

The IC$_{50}$ values of the test compounds were determined by plotting compound concentration versus cell viability.

The following compounds (Cooper. N., et al., *Chem. Commun.*, 16, 1764-1765 (2002) and WO 00/12508) were tested as comparisons:

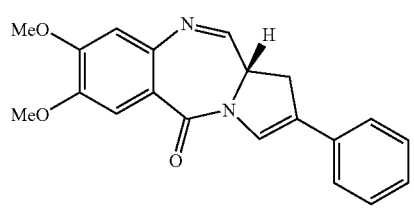

C1

-continued

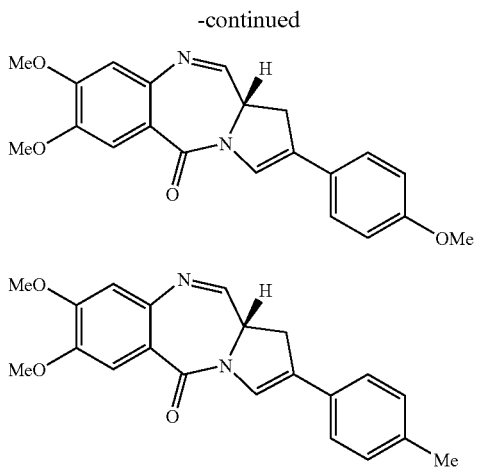

The results are as shown in the following tables.

TABLE 1

Breast MACL MCF7

| Compound | IC$_{50}$ (nM) |
| --- | --- |
| C1 | 19.33 |
| C2 | 1.96 |
| C3 | 1.59 |
| 11 | 0.22 |
| 13 | 0.26 |
| 15 | 0.15 |
| 19 | 0.35 |
| 21 | <0.1 |
| 23 | 0.35 |

TABLE 2

Renal RXF 944L

| Compound | IC$_{50}$ (nM) |
| --- | --- |
| C1 | 20.50 |
| C2 | 1.50 |
| C3 | 0.89 |
| 17 | 0.17 |
| 21 | <0.1 |

TABLE 3

Lung 629L

| Compound | IC$_{50}$ (nM) |
| --- | --- |
| C1 | 44.50 |
| C2 | 5.00 |
| C3 | 8.00 |
| 19 | 1.00 |
| 21 | 0.36 |

TABLE 4

Melanoma MEXF 462NL

| Compound | IC$_{50}$ (nM) |
| --- | --- |
| C1 | 40.00 |
| C2 | 2.85 |
| C3 | 2.00 |
| 21 | <0.1 |

NCI In Vitro Cytotoxicity Studies

The National Cancer Institute (NCI), Bethesda, Md. USA has available an in vitro cytotoxicity screen which consists of approximately 60 human tumour cell lines against which compounds are tested at a minimum of five concentrations each differing 10-fold. A 48 hour continuous exposure protocol is used, where cell viability or growth is estimated with an SRB protein assay.

Method

The test compounds were evaluated against approximately 60 human tumour cell lines. The NCI screening procedures were described in detail by Monks and co-workers (Monks, A et al., Journal of the National Cancer Institute, 1991, 83, 757). Briefly, cell suspensions were diluted according to the particular cell type and the expected target cell density (5000-40,000 cells per well based on cell growth characteristics), and added by pipette (100 µL) into 96-well microtitre plates. The cells were allowed a preincubation period of 24 hours at 37° C. for stabilisation. Dilutions at twice the intended test concentration were added at time zero in 100 µL aliquots to the wells. The test compounds were evaluated at five 10-fold dilutions ($10^{-4}$, $10^{-5}$, $10^{-6}$, $10^{-7}$ and $10^{-8}$ µM). The test compounds were incubated for 48 hours in 5% $CO_2$ atmosphere and 100% humidity. The cells were then assayed using the sulphorhodamine B assay. A plate reader was used to read the optical densities and a microcomputer processed the readings into GI$_{50}$ values (in Moles), which is the dosage required to limit cell growth to 50%.

The results of these studies can be summarized by averaging log GI$_{50}$ across all the cell lines tested to derive a MG_MID value, which shows that compound 25 (MG_MID=−7.18) is more effective than compound 23 (MG_MID=−6.34).

NCI Hollow Fibre Assay for Preliminary In Vivo Testing

The Biological testing Branch of the Developmental Therapeutics Program of the NCI has adopted a preliminary in vivo screening tool for assessing the potential anticancer activity of compounds identified by the large scale in vitro cell screen. For these assays, human tumour cells are cultivated in polyvinylidene (PVDF) hollow fibres, and a sample of each cell line is implanted into each of two physiologic compartments (intraperitoneal and subcutaneaous) in mice. Each test mouse received a total of 6 fibres (3 intraperitoneally and 3 subcutaneously) representing 3 distinct cancer cell lines. These mice are treated with potential antitumour compounds at each of 2 test doses by the intraperitoneal route using a QD×4 treatment schedule. Vehicle controls consist of 6 mice receiving the compound diluent only. The fibre cultures are collected on the day following the last day of treatment. To assess anticancer effects, the viable cell mass is determined for each of the cell lines using a formazyn dye (MTT) conversion assay. From this, the % T/C can be calculated using the average optical density of compound treated samples divided by the average optical; density of the vehicle controls. In addition, the net increase in cell mass can be determined for each sample, as a sample of fibre cultures are assessed for viable cell mass on the day of implantation into mice. Thus, the cytostatic and cytocidal capacities of the test compound can be assessed.

Generally, each compound is tested against a minimum of 12 human cancer cell lines. This represents a total of 4 experiments since each experiment contains 3 cell lines. The data are reported as % T/C for each of the 2 compound doses against each of the cell lines with separate values calculated for the intraperitoneal and subcutaneous samples.

Compounds are selected for further in vivo testing in standard subcutaneous xenograft models on the basis of several hollow fibre assay criteria. These include: (1) a % T/C of 50 or less in 10 of the 48 possible test combinations (12 cell lines×2 sites ×2 compound doses); (2) activity at a distance (intraperitoneal drug/subcutaneous culture) in a minimum of 4 of the 24 possible combinations; and/or (3) a net cell kill of 1 or more of the cell lines in either implant site. To simplify evaluation, a points system has been adopted which allows rapid evaluation of the activity of a given compound. For this, a value of 2 is assigned for each compound dose which results in a 50% or greater reduction in viable cell mass. The intraperitoneal and subcutaneous samples are scored separately so that criteria (1) and (2) can be evaluated. Compounds with a combined IP+SC score of 20, a SC score of 8 or a net cell kill of one or more cell lines are referred for xenograft testing. This comparison indicated that there was a very low probability of missing an active compound if the hollow fibre assay was used as the initial in vivo screening tool. In addition to these criteria, other factors (e.g. unique structure, mechanism of action) may result in referral of a compound for xenograft testing without the compound meeting these criteria.

Certain compounds of the invention were tested in variations of these assays, to assess their activity against renal and melanoma cell lines. In the melanoma assay, only 6 cell lines are used, and therefore compounds with a combined IP+SC score of 10 or a SC score of 4 are referred for xenograft testing. In the renal assay, only three cell lines are used and therefore compounds with a combined IP+SC score of 5 or a SC score of 2 are referred for xenograft testing.

The results of this assay are presented below in tables 5 and 6, including results for some of the compounds disclosed in Cooper. N., et al., *Chem. Commun.*, 16, 1764-1765 (2002) and WO 00/12508:

TABLE 5

| Compound | Renal | | |
|---|---|---|---|
| | IP | SC | IP + SC |
| C1 | 0 | 0 | 0 |
| C3 | 2 | 0 | 2 |
| 13 | 4 | 2 | 6 |
| 27 | 4 | 4 | 8 |

TABLE 6

| Compound | Melanoma | | |
|---|---|---|---|
| | IP | SC | IP + SC |
| C1 | 4 | 0 | 4 |
| C3 | 0 | 2 | 2 |
| 13 | 2 | 4 | 6 |
| 19 | 4 | 4 | 8 |
| 21 | 10 | 0 | 10 |

On the basis of these results, compounds 13 and 27 have been selected to be tested in the next stage of the NCI program (xenografts) on renal cancers, whilst compounds 12 and 21 have been selected to be tested on melanomas.

The invention claimed is:

1. A compound of formula (I):

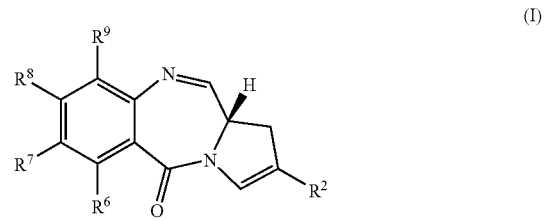

or pharmaceutically acceptable salts, or solvates thereof, wherein: $R^6$, $R^7$ and $R^9$ are independently selected from H, R, OH, OR, SH, SR, $NH_2$, NHR, NRR', nitro, $Me_3Sn$ and halo;

where R and R' are independently selected from $C_{1-7}$ alkyl, heterocyclyl having 3 to 20 ring atoms of which 1 to 10 are ring heteroatoms independently selected from the group consisting N, O and S and aryl or heteroaryl having 5 to 20 ring atoms, the heteroaryl groups having one or more heteroatoms independently selected from the group consisting of N, O and S; $R^8$ is selected from H, R, OH, OR, SH, SR, $NH_2$, NHR, NRR', nitro, $Me_3Sn$ and halo, or the compound is a dimer with each monomer being of formula (I), where the $R^8$ groups of each monomers form together a dimer bridge having the formula —X—R''—X— linking the monomers, where R'' is a $C_{3-12}$ alkylene group, which chain may be interrupted by one or more heteroatoms selected from the group consisting of O, S, and NH, and/or aromatic rings selected from the group consisting of benzene and pyridine, and each X is independently selected from O, S, or NH;

or any pair of adjacent groups from $R^6$ to $R^9$ together form a group —O—$(CH_2)_p$—O—, where p is 1 or 2; and $R^2$ is a napthyl group, optionally substituted by one or more substituents selected from the group consisting of halo, $C_{1-7}$ alkyl, $C_{1-7}$ alkoxy, heterocyclyl having 3 to 20 ring atoms of which 1 to 10 are ring heteroatoms independently selected from the group consisting N, O and S and aryl or heteroaryl having 5 to 20 ring atoms, the heteroaryl groups having one or more heteroatoms independently selected from the group consisting of N, O and S.

2. A compound according to claim 1, wherein $R^9$ is H.

3. A compound according to claim 1, wherein $R^6$ is H.

4. A compound according to claim 1, wherein $R^7$ and $R^8$ (when the compound is not a dimer) are selected from OMe and $OCH_2Ph$.

5. A pharmaceutical composition containing a compound of claim 1, and a pharmaceutically acceptable carrier or diluent.

6. A method of treatment of melanomas, or breast, renal, or lung cancer, comprising administering to a subject in need of treatment a therapeutically-effective amount of a compound of claim 1.

7. A compound of formula (II)

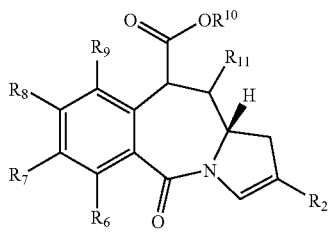

wherein $R^2$ is a napthyl group, optionally substituted by one or more substituents selected from the group consisting of halo, $C_{1-7}$ alkyl, $C_{1-7}$ alkoxy, heterocyclyl having 3 to 20 ring atoms of which 1 to 10 are ring heteroatoms independently selected from the group consisting N, O and S and aryl or heteroaryl having 5 to 20 ring atoms, the heteroaryl groups having one or more heteratoms independently selected from the group consisting of N, O and S;

$R^6$, $R^7$ and $R^9$ are independently selected from H, R, OH, OR, SH, SR, $NH_2$, NHR, NRR', nitro, $Me_3Sn$ and halo;

$R^8$ is selected from H, R, OH, OR, SH, SR, $NH_2$, NHR, NRR', nitro, $Me_3Sn$ and halo, or the compound is a dimer with each monomer being of formula (II), where the $R^8$ groups of each monomers form together a dimer bridge having the formula —X—R"—X— linking the monomers, where R" is a $C_{3-12}$ alkylene group, which chain may be interrupted by one or more heteroatoms selected from the group consisting of O, S, and NH, and/or aromatic rings selected from the group consisting of benzene and pyridine, and each X is independently selected from O, S, or NH;

or any pair of adjacent groups from $R^6$ to $R^9$ together form a group —O—$(CH_2)_p$—O—, where p is 1 or 2;

$R_{10}$ is selected from:
(a) 4—$NO_2$—$C_6H_4$—$CH_2$—;
(b) 2—$NO_2$—, 4,5-diMeO—$C_6H_4$—$CH_2$;
(c) $C_6H_5$—$CH_2$—; and
(d) Me—$SO_2$—$C_2H_4$—;

$R_{11}$ is selected from OH, OR or SR; and

R and R' are independently selected from $C_{1-7}$ alkyl, heterocyclyl having 3 to 20 ring atoms of which 1 to 10 are ring heteroatoms independently selected from the group consisting N, O and S and aryl or heteroaryl having 5 to 20 ring atoms, the heteroaryl groups having one or more heteratoms independently selected from the group consisting of N, O and S.

* * * * *